United States Patent [19]

Riederer

[11] Patent Number: 4,542,459
[45] Date of Patent: Sep. 17, 1985

[54] MATCHED FILTER FOR X-RAY HYBRID SUBTRACTION

[75] Inventor: Stephen J. Riederer, Wauwatosa, Wis.

[73] Assignee: General Electric Company, Schenectady, N.Y.

[21] Appl. No.: 444,953

[22] Filed: Nov. 26, 1982

[51] Int. Cl.⁴ ............................................. G06F 15/42
[52] U.S. Cl. ........................................ 364/414; 378/5; 378/99; 378/901; 358/111
[58] Field of Search ................... 364/414; 250/363 S; 378/99, 5, 901, 11, 12; 358/111

[56] References Cited

U.S. PATENT DOCUMENTS

| | | | |
|---|---|---|---|
| 4,029,963 | 6/1977 | Alvarez et al. | 378/5 X |
| 4,335,427 | 6/1982 | Hunt et al. | 364/414 |
| 4,350,998 | 9/1982 | Verhoeven | 358/111 |
| 4,355,331 | 10/1982 | Georges et al. | 378/99 |
| 4,437,161 | 3/1984 | Anderson | 364/414 |
| 4,445,226 | 4/1984 | Brody | 378/5 X |
| 4,450,478 | 5/1984 | Ledley | 364/414 X |
| 4,456,926 | 6/1984 | Kruger et al. | 358/111 |
| 4,463,375 | 7/1984 | Macovski . | |

Primary Examiner—Jerry Smith
Assistant Examiner—Louis Woo
Attorney, Agent, or Firm—Fuller, House & Hohenfeldt

[57] ABSTRACT

Low and high energy x-ray exposures are made before and after an injected x-ray contrast medium arrives at a blood vessel of interest. In one mode, low and high energy mask images are made and these are subtracted from subsequent low and high energy images, respectively, to yield temporal difference images. The projected intensities of the contrast medium with respect to time constitute matched filter coefficients by which the difference images are mulitplied. The matched filtered images are summed, multiplied by weighting factors and subtracted from each other to yield a final hybrid image. In an alternative mode, successive pairs of low and high energy images are subtracted to yield energy difference images. The difference images are subjected to matched filtering and summed and the results subtracted to produce a final hybrid image. The matched filter coefficients are selected so the dc component in the image signal is equal to zero so everything that is constant in the initial series of images cancels out by subtraction and only contrast medium signal remains.

43 Claims, 19 Drawing Figures

MATCHED FILTER FOR X-RAY HYBRID SUBTRACTION

BACKGROUND OF THE INVENTION

The invention is in a field which is now commonly designated as digital subtraction angiography. The invention disclosed herein pertains to methods and apparatus for performing hybrid subtraction of x-ray images which results in a high ratio of the signals representative of the subtracted images to noise. More specifically, the invention pertains to maximizing image representative signals relative to noise by using matched filter methods and apparatus.

A matched filter for x-ray temporal subtraction is described and claimed in pending application Ser. No. 358,741, filed Mar. 15, 1982. Hybrid subtraction methods and apparatus are disclosed and claimed in pending application Ser. No. 271,683, filed Apr. 26, 1982. Both of the aforementioned applications are assigned to the assignee of this application. The basic hybrid subtraction method and apparatus for performing the same are described in pending patent application Ser. No. 260,694, filed May 5, 1981 wherein W. R. Brody is the inventor.

Temporal subtraction is one well known procedure for enhancing visualization of blood vessels to the exclusion of surrounding soft tissue and bony structures. In temporal subtraction, an x-ray image of the blood vessels in a region of interest in the body is acquired just before an opaque x-ray contrast medium, such as an iodinated compound, that has been injected in the circulatory system arrives in the vessels of interest. This is called a pre-contrast mask image and it contains the vessels and usually a background of soft tissue and bony structures. The precontrast mask image is digitized and the digital data representative of the picture elements (pixels) in the image are placed in a digital frame memory. When the contrast medium reaches the vessels in the region of interest, a series of x-ray images are made and they are converted to digital data. The mask or pre-contrast image data are then subtracted from the post-contrast image data to cancel or subtract out all soft tissue and bony structure and anything that is common to both images to thereby enhance visualization of the blood vessels that contain the contrast medium. Usually the x-ray tube current and applied kilovoltages are the same for the pre-contrast and post-contrast images. The method is called temporal subtraction imaging because of the substantial time lapse between the pre-contrast and post-contrast images. As is known, the pre-contrast mask images and post-contrast images will always have some noise content that is introduced by the x-ray system and the electronic components that are used to generate and process the signals that represent the image.

Temporal subtraction provides high signal-to-noise ratio (SNR) and is a preferred procedure in cases where there is little if any movement of soft tissue during the interval between acquisition of the pre-contrast and post-contrast images. However, where there is tissue motion there must necessarily be information that is not common to successive images so this information does not cancel out by subtraction and contrast of the contrast mediumfilled vessel and the surrounding residual tissue is diminished. Blood vessel and surrounding tissue movement is likely to exist in abdominal vessel studies were peristalsis of the digestive organs moves the vessels. Renal artery studies are often adversely affected. Movement is also exhibited in carotid artery studies where the swallowing reflex causes an artifact which can obscure perception of the vessels of interest.

Another image subtraction procedure is characterized as energy subtraction. Energy subtraction is based on the fact that x-ray attenuation by a body or any material is an x-ray energy dependent phenomenon and that the energy dependence is different for materials having different atomic number averages. In energy subtraction, an x-ray image of a region of interest in the body is obtained with a nominally low kilovoltage (kV) applied to the x-ray tube so the beam projected through the body has an energy spectral distribution within a band having low average energy. After a low average energy image is obtained and digitized, at least one more image is obtained with a comparatively higher kV applied to the x-ray tube and a resulting higher average energy spectral band. For ordinary tissue studies the two images may be made in the absence of any contrast medium. For angiographic studies, the two images are obtained when there is an x-ray contrast medium such as an iodinated compound present in the blood vessels. In any case, the high average energy image pixel data are subtracted from the low average energy pixel data and a difference image remains. Prior to subtraction, the data are usually variously weighted or scaled to bring about cancellation of soft tissue. The data could be scaled to eliminate bone from the difference image instead of tissue. However, it is not possible to remove or cancel bony structures without also removing most of the iodinated contrast medium which is really what one is trying to visualize in angiographic studies since it defines the interior shape of the vessel.

There are also brightness monuniformities in the subtracted or difference images due to several effects when the data are acquired using an image intensifier that is coupled to a television camera. Veiling glare, which is like haze, results from light diffusion or scattering often present in the input or output phosphors of the image intensifier. The fact that rays of a broad x-ray beam are scattered by body tissue in an energy dependent manner between ray paths also causes loss of contrast in the difference image. Differential detection of x-rays at various energies in the input phosphor of the image intensifier leads to additional brightness nonuniformities. None of these phenomena can be completely nullified by energy subtraction alone.

Hybrid subtraction has been proposed for cancelling the contrast of stationary bone and soft tissue and elimination of artifacts due to soft tissue motion while still providing an image of the contrast medium filled vessels. Hybrid subtraction procedures use a combination of energy and temporal subtraction methods. In hybrid subtraction, x-ray images are obtained using two x-ray spectra having different average energies and are combined in a manner to suppress signals due to soft tissue in a heterogeneous object such as the body. Basically, in hybrid subtraction, a mask image is obtained first by projecting a low average energy x-ray beam (hereafter called low energy beam or low energy spectral band) through the body followed by a higher average energy x-ray beam (hereafter called high energy beam or high energy spectral band) when the injected x-ray contrast medium has not yet entered the blood vessels in the anatomical region of interest. The images, consisting primarily of bone and soft tissue acquired at two energies, are scaled and weighted using appropriate constants and then subtracted to produce a mask image in which signals due to soft tissue variations are suppressed or cancelled and bony structures remain. The data for a pair of high and low energy x-ray images are next obtained when the injected contrast medium reaches the vessels in the region of interest. The data for this pair of images are acted upon by the same constant weighting factors that are used with the first pair of images to cancel soft tissue. One image acquired in this exposure pair is subtracted from the other such that the resulting post-contrast image contains data representative of bone structures plus vessels containing contrast medium. The final step in hybrid subtraction is to subtract the dual energy post-contrast difference image from the dual energy pre-contrast mask difference image to thereby suppress or cancel the bone structures and isolate the contrast medium-containing vessels. A major advantage of hybrid subtraction over temporal subtraction alone is the reduced sensitivity to soft tissue motion artifacts because the soft tissue is suppressed or cancelled in the pre-contrast and post-contrast dual energy images.

Hybrid subtraction is superior for eliminating soft tissue structures that may have moved during the time between obtaining the mask image and post-contrast image or images. As indicated earlier, however, if there is no movement ordinary temporal subtraction is preferred because of its better SNR compared to hybrid subtraction.

Scattering of the x-ray beam by the body is also considered. Scatter in an image depends on x-ray beam energy, beam path length and the density of the object being penetrated. In hybrid subtraction the scattering that results from use of a wide area x-ray beam is of little consequence since scatter is essentially the same for each energy subtracted pair of images. Hence, scatter effects on image brightness nonuniformities are subtracted out when the dual energy difference image pairs are subtracted.

In hybrid subtraction as presently practiced, the multiple subtractions resulting from subtracting pre-contrast high and low x-ray energy images to obtain a first difference image and subtracting low and high x-ray energy post-contrast images to obtain a second energy subtracted difference image and then subtracting the two difference images results in a substantial reduction of the signal-to-noise ratio. To compensate for the decreased signal-to-noise ratio of hybrid subtraction imaging compared to temporal subtraction imaging, generally the x-ray tube current has to be increased or exposure times have to be increased or both. In such cases the time between the mid-points of the low and high pre-contrast and post-contrast x-ray exposures may have to become very long and this means that the energy subtracted images themselves may have some motion artifact which is the exact effect the hybrid subtraction method is supposed to suppress. It will be evident then that hybrid subtraction as presently constituted involves a balancing of efficient x-ray dose utilization, motion artifact reduction, and signal-to-noise ratio, none of which have been optimized until the invention disclosed herein was made.

Recursive filtering has been proposed for reducing the effect of noise in temporally subtracted x-ray images, that is, in the difference image that results from subtracting a mask image obtained at one time from a live contrast medium exhibiting image obtained shortly thereafter. Recursive filtering is discussed at length in previously cited pending application Ser. No. 358,741. Recursive filtering in temporal subtraction systems but not in hybrid subtraction systems was recently described in several articles: Kruger, R. A. "A Method for Time Domain Filtering Using Computerized Fluoroscopy": *Medical Physics,* Vol. 8, No. 4, July/August 1981, pp. 465-469; Kruger, R. et al, "Time Domain Filtering Using Computerized Fluoroscopy—Intravenous Angiography Applications", SPIE Vol. 314 Digital Radiography (1981), pp. 319-326; Gould, R. G. et al "Investigation of a Video Frame Averaging Digital Subtraction System," SPIE Vol. 314, pp. 184-190 (1981); and Gould, R. G. et al "A Digital Subtraction System with Tandem Video Processing Units," SPIE Vol. 273, pp. 125-132 (1981).

SUMMARY OF THE INVENTION

A primary object of the present invention is to obviate the two limitations of the hybrid subtraction sequence cited above; namely, inefficient use of x-ray dosage and poor signal-to-noise ratio in the difference image compared to temporal subtraction. The problems of hybrid subtraction are solved, in accordance with the invention, by using matched filtering in conjunction with dual x-ray energy image subtraction techniques.

It is known in the signal processing art that if a useful signal of known shape is present in a noisy total signal or waveform, then the maximum useful signal-to-noise ratio is attained if the noisy waveform is correlated with a function "h" matching the known shape of the useful signal. There is usually a different value $h_t$ of the function for every point in time over the useful signal interval.

In accordance with the invention matched filtering is based on the recognition that the concentration or density and, hence, projected intensity of an x-ray contrast medium that flows into a blood vessel from its injection site is a function of time. In the hybrid x-ray image subtraction process the contrast medium defines and permits visualization of the interior of the blood vessel in the region of interest. The unwanted non-useful part of the image representing signals comprise various kinds of noise arising in the electronics and x-ray image acquisition system. Unwanted signal also includes that which represents bony structures and soft tissue, especially soft tissue that has moved between x-ray exposures, since these signal components can only obscure the image of the blood vessel that is defined by the contrast medium. In the present invention matched filtering is implemented in a fashion that not only reduces noise but in addition cancels or subtracts out anything that remains constant in a sequence of images obtained by making a succession of low and high energy x-ray exposures. Cancellation of everything that remains constant in a long sequence of images results from the fact that, in accordance with the invention, the filtered signal representing the final hybrid subtraction image has a steady state or dc component equal to zero.

Briefly stated, in accordance with the invention, two different procedures are disclosed for obtaining a sequence of x-ray images that, respectively, yield signals or data representative of a hybrid subtraction image and that can be used to display the blood vessel of interest on a television screen. Matched filter schemes appropriate to the order in which the x-ray exposures are made and to how the signals representing the images are preprocessed is also disclosed. In addition, a matched filter scheme in the nature of recursive filtering is disclosed.

One of the hybrid subtraction modes employing matched filtering involves making a sequence of alternate low x-ray energy and high x-ray energy exposures beginning at a time when an x-ray contrast medium that has been injected into the body's circulatory system has not yet reached the blood vessel of interest and continuing through the time during which the contrast medium is present in the vessel and for a short time thereafter. Analog video signals representative of the individual image frames are digitized. In this case temporal subtraction procedures are used first. The first low energy image is treated as a mask image. Every subsequent low energy image is subtracted from the first low energy (low mask) image and the sequence of difference images resulting from the respective subtractions is stored on video disk. Likewise, each subsequent high energy image is subtracted from the first high energy (high mask) and the sequence of difference images resulting from the respective subtractions is stored on video disk. So at the end of an exposure sequence there are stored on disk a series of alternating low and high energy temporal difference images. The low energy temporal difference images are read off of the disk and displayed on a television monitor after an exposure sequence is completed. Everything that is constant in the low energy mask and any ensuing low energy image would ordinarily have been subtracted out except for the contrast medium. That is, soft tissue and bone would ordinarily be subtracted out and the image that exhibits the best definition and intensity of the contrast medium would be used for diagnostic purposes.

No temporal difference image is likely to be fully satisfactory if there has been soft tissue movement during the exposure sequence due to swallowing or peristalsis for instance. In such cases reprocessing of the stored difference image data is undertaken wherein hybrid subtraction is accomplished and, in accordance with the invention, the image data are subjected to matched filtering.

In an alternative hybrid subtraction mode the x-ray exposure sequence is basically the same as in the mode just outlined. That is, a sequence of low and closely successive high energy exposure pairs are obtained before the contrast medium reaches the vessels of interest and continously through the interval when the contrast medium is present and for an interval after the contrast medium has cleared out of the region of interest. In this mode energy subtraction is performed concurrently with image acquisition. Every low energy image and the next closely successive high energy image are subtracted. The difference image data resulting from the successive subtractions are stored on video disk as the subtractions are made so there will be a series of energy subtracted images stored after an x-ray exposure sequence is completed. In this mode temporally subtracted images are not immediately available for display since only energy subtracted images are in storage. A reprocessing procedure is used which results in combining energy subtraction with temporal subtraction as is required for accomplishing hybrid subtraction and, in accordance with the invention, the images are subjected to matched filtering in the course of reprocessing.

Also discussed herein is a method and apparatus for recursive filtering of images obtained with a sequence of high and low x-ray exposure pairs.

A more detailed description of hybrid subtraction and matched filtering methods and apparatus will now be set forth in reference to the drawings.

DESCRIPTION OF A PREFERRED EMBODIMENT

Figure 1:
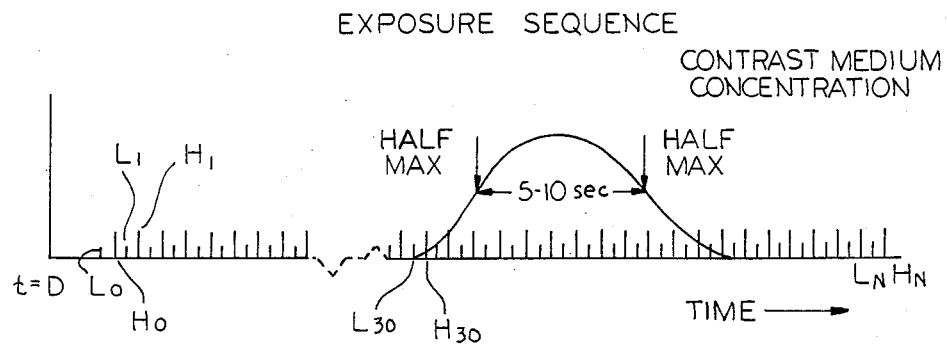
FIG. 1 shows the x-ray exposure sequence used for various dual x-ray energy, hybrid subtraction matched filter methods.

FIG. 1 shows the dual x-ray energy exposure sequence that may be used for any of the hybrid subtraction matched filter or recursive filter methods described herein.

Figure 9:
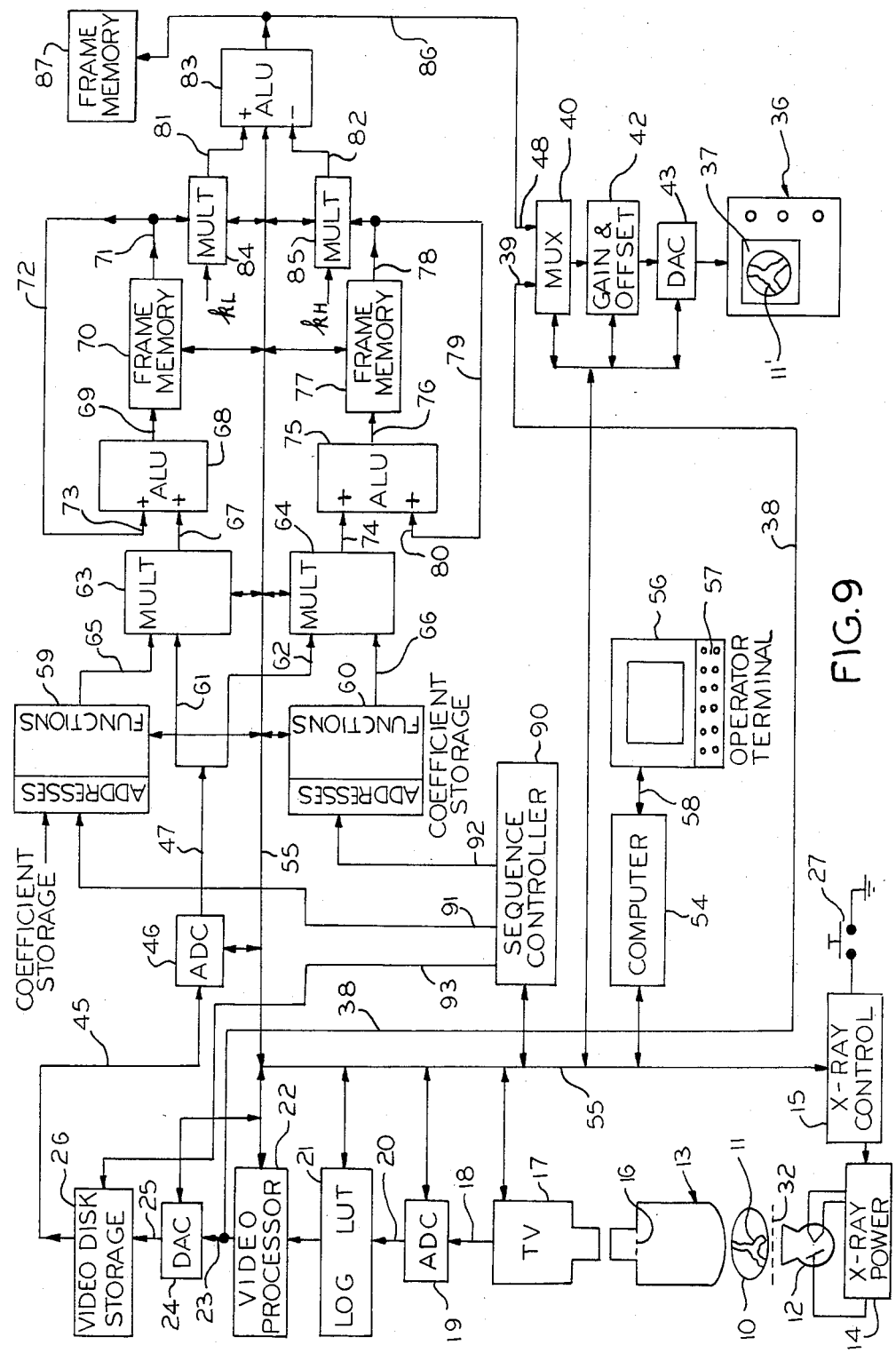
FIG. 9 is a diagram of the hardware used for conducting the matched filter hybrid subtraction methods described herein.

Before discussing FIG. 1, however, attention is invited to the FIG. 9 schematic hardware diagram for a brief review of the apparatus for making the x-ray exposures.

In the left region of FIG. 9 the patient undergoing an angiographic examination is represented by the ellipse 10. A blood vessel of interest is marked 11. An x-ray tube 12 is located on one side of the patient and an x-ray image intensifier 13 is located on the other side. The x-ray tube power supply is symbolized by the block marked 14 and the control for the supply by the block 15. The x-ray control has the capability of switching the power supply so it will apply alternating relatively low kilovoltage such as about 85 kilovolts peak (kVp) between the anode and cathode of the x-ray tube 12 for short exposure intervals on the order of a television frame time and relatively higher applied kVp such as about 130 kVp for short exposure intervals. The low and high kilovoltages are applied alternatingly during an entire exposure sequence which for the purpose herein may contain forty low kilovoltage x-ray beam pulses alternated with forty high kilovoltage beam pulses by way of example and not limitation. The high voltage exposures in a pair could precede the low voltage exposure if desired. The only requirement is that there be alternating lows and highs or highs and lows in a sequence.

When the low and high kilovoltages are applied to the x-ray tube the resulting x-ray beams are not composed of corresponding monoenergetic x-ray photons but there is a distribution of energies within a spectral band which has an average energy. Hence, for convenience the relatively low and high average energy exposures will simply be called low and high energy exposures herein.

In FIG. 9, the x-ray images resulting from projecting alternate low and high energy x-ray beams are converted to optical images which appear on the output phosphor 16 of the image intensifier tube 13. A television (TV) camera 17 views the optical images and converts each image frame to analog video signals which are transmitted by way of a line 18 to an analog-to-digital converter (ADC) 19. ADC 19 converts the analog video signals to digital signals, usually 10-bits wide, whose values correspond to the intensities of the picture elements (pixels) that compose an image frame. The digitized pixels are input by way of a line 20 to a logarithm look-up table (log LUT) 21 where the pixels are converted to corresponding logarithmic values and amplified. The logarithmically expressed digital pixel values are input by way of a line 22 to a digital video processor 22 whose functions will be elaborated later.

In the embodiment described herein, data representative of images are converted to logarithmic values and amplified substantially concurrently with image acquisition. Thus, further signal processing and, particularly, subtraction of images is performed with logarithmic data. It should be understood, however, that the signals or data representative of images may be amplified, subtracted and otherwise processed using linear signal processing methods as well. Moreover, although in the preferred procedure described herein, the image data are converted to logarithmic form shortly after the data are acquired from the video camera 17, the conversion could take place at other times as well.

One output bus 23 from processor 22 is input to a digital-to-analog converter (DAC) 24 wherein digital data representative of image frames that may have been variously processed are converted to analog video signals again and transmitted over line 25 for storage on video disk storage that is symbolized by the block marked 26. It would be permissible to store the video signals in digital signal form in a storage device 26 in which case the output of processor 22 would be coupled directly to the input of storage device 26.

Now return to FIG. 1 for a discussion of the x-ray exposure sequence that is used for image acquisition in contemplation of executing any of the hybrid subtraction and matched filtering or recursive filtering modes that are to be described herein. In any case assume that everything is in readiness for conducting an angiographic examination and at time zero (t=0) an x-ray opaque medium is injected into the patient's circulatory system remote from the blood vessel that is desired to be visualized. Shortly thereafter, while the opaque medium is on its way to the vessel of interest, the series of alternate low and high energy x-ray exposures is initiated. The first low energy exposure is designated by $L_0$ and the first high energy exposure by $H_0$. The next low and high energy exposures are $L_1$ and $H_1$ and so on up to $L_N H_N$ where the x-ray pulses are discontinued. In this example, the x-ray contrast medium arrives in the blood vessel region of interest at about the time that the thirtieth low and high energy exposures ($L_{30}$ and $H_{30}$) are being made. Contrast medium concentration, represented by the curve having that label, increases for a time, reaches a peak, decreases for a time that is generally a little longer than its increasing time and finally it is displaced solely by blood again. Typically, contrast medium in some concentration may be present in the vessel for about twenty seconds and typically there will be 5 to 10 seconds between its half-maximum concentration or projected intensity levels.

The period between $L_0$ and the time the contrast medium begins to enter the vessel region of interest is called the pre-contrast period herein. The time during which some contrast medium is present in the vessel is called the post-contrast period and the following period ending with termination of the low and high energy x-ray pulse pairs is called the after-post-contrast period.

Making the series of alternate low and high energy x-ray exposures as in FIG. 1 and scanning or reading out the TV camera 17 image target after each exposure can be variously timed for the ultimate objective of employing matched filtering in hybrid subtraction. Some timing relationships are suggested in parts 5A to 5D of FIG. 5 wherein x-ray exposure pulse widths and TV camera target readout are plotted as a function of time.

In part 5A the low energy exposure is marked L and has a duration of 2 television frame times. The low energy x-ray pulse may occupy less than the full 2 TV frame times, if desired. Similarly, the actual high energy x-ray pulse width may be less than the one frame shown. Regardless of pulse width the time from the start of an exposure to video signal or TV target readout following an exposure is generally some integral number of TV frame times. This allows for exposure times longer than those shown in part 5A of FIG. 5. In a 60 Hz television system each frame time equals 1/30 of a second and in a 50 Hz system a frame time equals 1/25 of a second. Timing in this example will be based on a 60 Hz system. In part 5A one frame time 30 is allowed for TV camera target readout after the low energy exposure as indicated by the analog video signal marked L in the line designated TV readout. During the frame following low energy image readout a high energy exposure, H, is made and this is followed by TV camera readout during the frame time 31. The TV camera image target is read out in the progressive scan mode in the illustrated embodiment but the interlaced scan mode could be used. The chosen x-ray tube current and, hence, x-ray beam intensity for the high and low energy exposures depends on a number of factors that are known to those familiar with x-ray phenomena. For any of the timing relationships in parts 5A–5D of FIG. 5, the kVp applied to the x-ray tube anode is preferably in the range of 75-85 kVp for the low energy exposures and in the range of 125 to 135 kVp for the high energy exposures. The low energy beam is desirably filtered to remove x-rays having such low energy that they would not penetrate through the body. Thus, aluminum filtration can be used in the low energy x-ray beam. During the high energy x-ray pulses, a filter 27 that removes radiation substantially below the peak of the high average energy spectrum is inserted synchronously. Copper is one suitable filter material for the high energy beam and it can be inserted while the aluminum filter remains in the beam.

Figure 5:
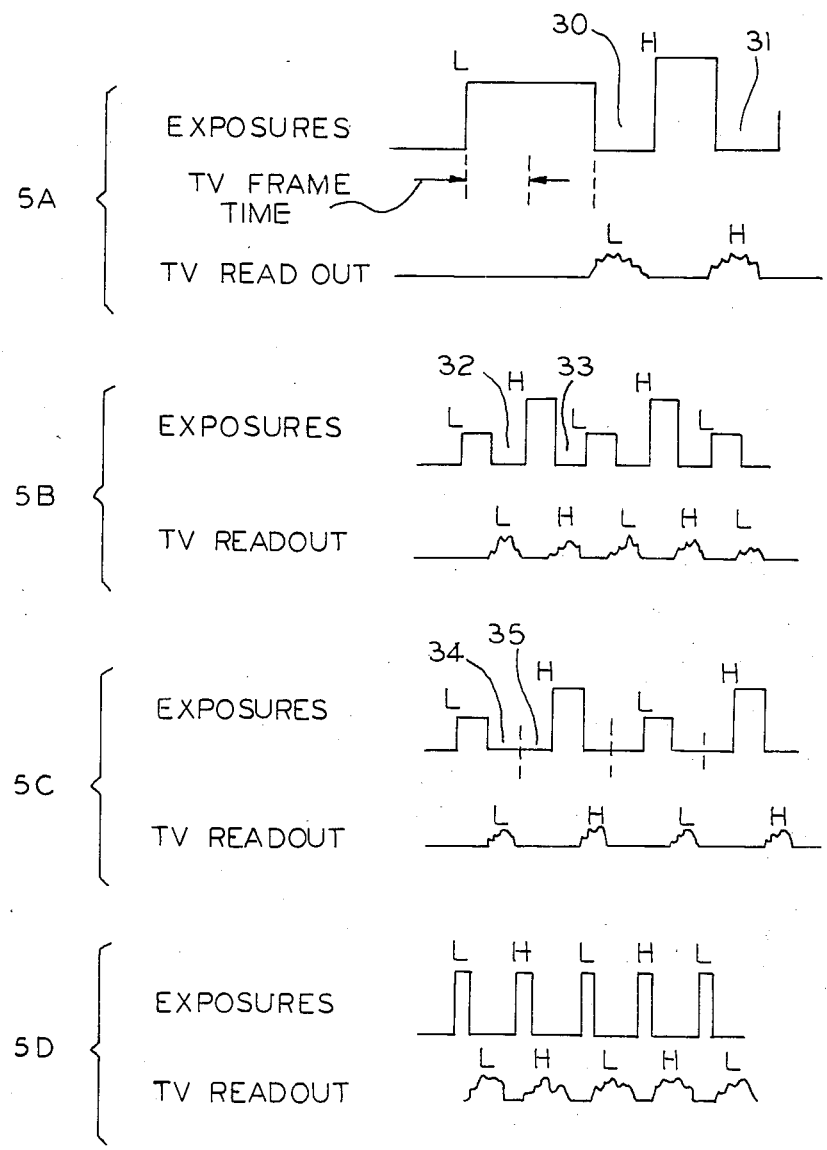
FIG. 5 shows in parts 5A–5D, some illustrative but not exclusive timing diagrams for various low x-ray energy and high x-ray energy exposure sequences in relation to television camera readout intervals.

In part 5A of FIG. 5 just described, each combination of successive low and high energy exposure pairs or readouts allows formation of one energy difference or energy subtracted image. Each pair uses five frame times or 5/30 of a second so if desired a maximum of six energy difference images per second are attainable. Body or soft tissue movement is likely to be insignificant between low and high energy exposures when one or even a few one-thirtieth second frame times elapse between them. In general, the exposure rate should be high enough to permit at least one but preferably more energy difference images per second.

Part 5B of FIG. 5 shows a timing sequence that has been used successfully and may be considered a preferred timing sequence. The low and high energy exposures are marked L and H, respectively. One television frame time is allotted for each exposure. TV camera progressive scan or target readout is performed during the single frame times 32 and 33 following the low and high energy frame times. This timing permits obtaining 7.5 energy subtracted or energy difference images per second.

Part 5C of FIG. 5 shows another timing sequence. Here, the low energy exposure, L, is made during a single television frame time and the high energy exposure, H, is made two frame times after the low. During the first frame time 34, for example, after a low and a high energy exposure too, the TV camera target is read out in the progressive scan mode. During the next frame time 35 or before the subsequent high energy exposure the TV camera target is scanned with the electron beam to scrub any residual signal from the previous exposure. This insures that any residual image from the low energy exposure is not read out. Similarly, the target may be scrubbed after each high energy exposure. Some TV camera targets are sticky and require scrubbing. Each combination of successive low and high energy readouts still forms one energy difference image. The part 5C timing format limits the number of available energy difference images to five per second.

Part 5D of FIG. 5 shows another timing format wherein the low, L, and high, H, energy exposures are of very short duration and are made during retrace time between successive television frames. Readout of the TV camera target is done during the frame times following each retrace period as shown in the line labelled TV readout. This format permits obtaining as high as fifteen energy difference images per second which is desirable for matched filtering in hybrid subtraction but it reaches the limits of the data handling speed of the signal processing system.

Exposure sequences other than those shown in parts 5A–5D of FIG. 5 are also permitted. For example, one could use a scrub frame 35 as in part 5C only following the low energy exposure target readout 34 and not use a similar scrub frame subsequent to the high energy exposure readout. In this case, if both the low and high x-ray energy pulse widths were less than one frame time then a rate of six energy-subtracted images per second would be allowed.

Likewise, as suggested earlier, image data acquisition need not be restricted to progessive mode video or TV camera target readout for each image frame. Interlaced or consecutive field readout could also be used provided exposure timing was set properly.

In at least one of the hybrid subtraction and matched filtering modes described hereinafter consecutive low and high energy images comprising a pair are subtracted from each other as the second live one in the pair is being acquired to thereby yield a succession of energy subtracted or energy difference images that are sent to storage. As will appear, it makes no difference whether the low energy exposures precede or follow the high energy image exposures. Either order is permissible. That is generally true of the various modes.

Basically, the hybrid image subtraction procedure as described in the earlier cited pending applications involves making at least one low and high x-ray energy exposure pair of pre-contrast images and multiplying the data representative of the images by suitable constants to bring about cancellation of soft tissue, but not bone, when the images are subtracted to produce a first energy difference mask image. At least one post-contrast pair of low and high energy images are also made and the data that represents them are multiplied by suitable constants to bring about cancellation of soft tissue but not bone nor the x-ray contrast medium when the images are subtracted to produce a second energy difference image. The first and second difference images are then subtracted on a temporal basis to bring about cancellation of bone and let the signals or data representative of the contrast medium filled blood vessel remain.

It can be shown that it makes no difference insofar as the final result is concerned whether the energy subtraction is done before the temporal subtraction or whether the pre-contrast and post-contrast low energy exposures are subtracted first to produce a first temporal difference image and the pre-contrast and post-contrast high energy images are subtracted next to produce a second temporal difference image. When the two temporal difference images are subtracted to yield the hybrid subtraction image the hybrid images will be the same for both orders of subtraction provided the multiplier constants are the same. In either case the hybrid image signal-to-noise ratio (SNR) will be lower than the image resulting from direct temporal subtraction. The new matched filter methods described hereinafter result in a improved SNR and are applicable to any order of energy and temporal subtractions.

One hybrid subtraction and matched filter mode, in accordance with the invention begins with making a series of low and high energy temporal difference images and storing them as on video storage disk 26 in FIG. 9 for instance. Matched filtering is done subsequent to image acquisition and uses the images that are in storage. The beginning of the procedure is described in reference to FIGS. 1 and 2.

Figure 2:
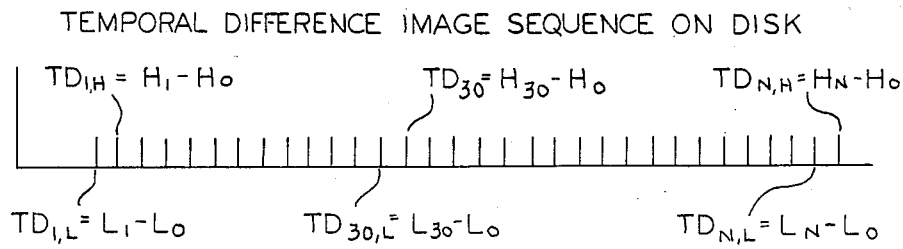
FIG. 2 is a diagram for explaining how in one operational mode temporal difference images are acquired and stored on video disk and subjected to energy subtraction and matched filtering retrospectively.

In FIG. 1 the series of low and high energy precontrast, post-contrast and after post-contrast images are made as is true in any case. FIG. 2 shows a case where a series of low and high temporal difference images are formed concurrently with the exposures. $L_0$ and $H_0$ are the first pre-contrast images in FIG. 1 and they are used as respective low and high energy mask images for obtaining the temporal difference image series in the FIG. 2 case. The logarithmic digital pixel data representative of the first low, $L_0$, and first high, $H_0$, pre-contrast image frames are stored concurrently with their acquisition in full frame memories, not shown, in video signal processor 22 of FIG. 9. Some predetermined time after $H_0$ occurs, $L_1$ exposure occurs and $L_0$ is subtracted from $L_1$ in the video processor 22 to yield the first low energy temporal difference image $TD_{1,L}$, which equals $(L_1-L_0)$ and is stored on disk. A second predetermined time after $L_1$ occurs, $H_1$ occurs and $H_0$ is subtracted from it to yield the second temporal difference image $TD_{1,H}$ which equals $(H_1-H_0)$ and is a high energy difference image which is stored on disk in analog video signal format. The process repeats alternatingly until the last low and high energy exposure pairs $L_N$ and $H_N$ occur. That is, every low energy pixel frame data $L_1$, $L_2 \ldots L_N$ has $L_0$ subtracted from it and the resulting low energy temporal difference image $TD_{N,L}$ are stored. And alternatingly every high energy pixel frame data $HD_1$, $H_2 \ldots H_N$ has $H_0$ subtracted from it and the resulting high energy temporal difference images $TD_{N,H}$ are stored on disk. The subscript N indicates the number of the temporal difference image and the subscripts L and H indicate respectively that it is a low or high energy image.

Thus, after the exposure sequence ends there is stored on disk a series of alternating low energy temporal difference images and high energy temporal difference images. The low energy temporal difference images data would have anything that is common to them such as bone and soft tissue subtracted out if there has been no patient movement during the sequence such that only contrast medium that defines the shape of the blood vessel would remain. All of the low energy temporally subtracted images can be displayed, on the television monitor 36 in FIG. 9 as the images are produced. The opaque vessel appearing on the screen 37 of TV monitor 36 is marked 11' whereas in body 10 it is marked 11. One display scheme involves transmitting the digital pixel signals that compose an image frame from an output of video processor 22 by way of a bus 38 to one input 39 of a digital signal multiplexer (MUX) 40. The output bus 41 of MUX 40 couples the digital data to circuitry represented by block 42 where signal gain is introduced to make sure the pixel signals will conform to the full dynamic range of the television monitor 36 and signal offset is introduced to obtain the desired gray scale. A digital-to-analog converter (DAC) 43 converts to analog video signals for driving TV monitor 36.

The low energy temporal difference images that are stored in analog video signal form on disk 26 in this embodiment rather than digital form can also be displayed or reviewed slowly one after another following the end of an exposure sequence. This review is for determining if any of the low energy temporal images, in which everything is subtracted out except the contrast medium, is free of artifacts caused by patient motion such that one or more might have satisfactory definition for diagnostic purposes. If satisfactory, hybrid subtraction and matched filtering become unnecessary. If there are motion artifacts, going ahead with hybrid subtraction and matched filtering is indicated.

In FIG. 9, readout of the analog video signals representing the low energy temporal difference images from disk 26 involves coupling the signals by way of a line 45 to the input of an analog-to-digital converter (ADC) 46 which converts the image frames to digital pixel values. The output bus 47 of ADC 46 leads into some circuitry which will be discussed later. For present purposes it is sufficient to say that the digital difference image pixel data is unaltered in this circuitry and eventually enters the other input 48 of MUX 40 after which gain and offset is inserted and conversion takes place in DAC 43 so analog video signals can drive TV monitor 36.

Assume that the low temporal difference images review reveals that all images are afflicted with artifacts or loss of definition due to soft tissue movement during the exposure sequence and, thus, hybrid subtraction and, in accordance with the invention matched filtering is indicated.

Expressed mathematically, the hybrid subtraction resulting image, R, can be expressed as follows:

$$R = k_L(L_M - L_0) - k_H(H_M - H_0) \qquad \text{(Eq. 1)}$$

where $L_M$ is any low energy image in the exposure sequence from which the low mask image, $L_0$, is subtracted to get the series of low energy temporal difference images, $TD_{M,L}$ which are stored. $H_M$ is any high energy image from which the high energy mask image, $H_0$, is subtracted to get the alternate series of high energy temporal difference images, $TD_{M,H}$, which are stored. $k_L$ and $k_H$ are the factors by which the low and high temporal difference images must be multiplied to effect material cancellation. The ratio $k_L/k_H$ is generally proportional to the ratio of the mass attenuation coefficients of the material to be cancelled for the high and low energy x-ray spectra, respectively. The ratio $k_L/k_H$ must change as different materials are to be cancelled.

At this time the temporally subtracted image sequence on disk can be designated as $$TD_{L1}, TD_{H1}, TD_{L2}, TD_{H2}, \ldots TD_{LN}, TD_{HN}$$

For hybrid subtraction and matched filtering each of the low temporal difference images must be multiplied, respectfully, by the respective values of a matched filter function $(h_{Li})$, where i indicates the low difference image number, and the results of the multiplication must be summed to produce $S_L$ (the sum of the matched filtered temporal difference images). The matched filter, h, corresponds generally to a plot of the projected intensity of the contrast medium bolus as a function of time but modified to have an average value of zero. The values of the function at the time any difference image is acquired are what the corresponding difference images are multiplied by. The summed image $S_L$ will be stored in frame memory 70 of FIG. 9 and will be used in the final hybrid subtraction step as will be discussed in detail later. Likewise, the high temporal difference images are multiplied, respectively, by unique matched filter, $h_{Hi}$, values and the results of the multiplications are summed to produce $S_H$ (the sum of the matched filtered high energy temporal difference images). The sum $S_H$ will be stored in frame memory 77 of FIG. 9 for further processing.

Next the sum $S_L$ from memory 70 is multiplied by the previously mentioned weighting coefficient $k_L$. This is actually done with a MULT 84 shown in FIG. 9. Likewise, the sum $S_H$ from memory 77 is multiplied by the weighting coefficient $k_H$ is a MULT 85 in FIG. 9. The matched filtered hybrid image, MF, results from taking the difference between the two weighted sums, thus:

$$MF = \left[ k_L \left( \sum_{i=1}^{N} h_{Li} TD_{i,L} \right) \right] - \left[ k_H \left( \sum_{i=1}^{N} h_{Hi} TD_{i,H} \right) \right] \quad \text{(Eq. 2)}$$

where the values of the function $h_{Li}$ and $h_{Hi}$ are equal to each other for the low and high energy temporal difference images to which they correspond. The terms in the brackets of Equation 2 are subtracted in the ALU 83 in FIG. 9 and the final hybrid subtracted match filtered image MF is output from ALU 83 on digital bus 86 for displaying of the image. The digital matched filtered hybrid image data is also stored in some type of memory so the image can be displayed continuously or accessed when desired. The memory is symbolized by the frame memory marked 87 but this could be a magnetic disk, not shown, or other storage medium.

In order for everything that is constant among the images in the sequence to cancel out or, in other words, in order to get a dc component in the matched filter MF final image equal to zero the sum of all of the low or high matched filter multiplier values h, (t) must equal zero.

Figure 7:
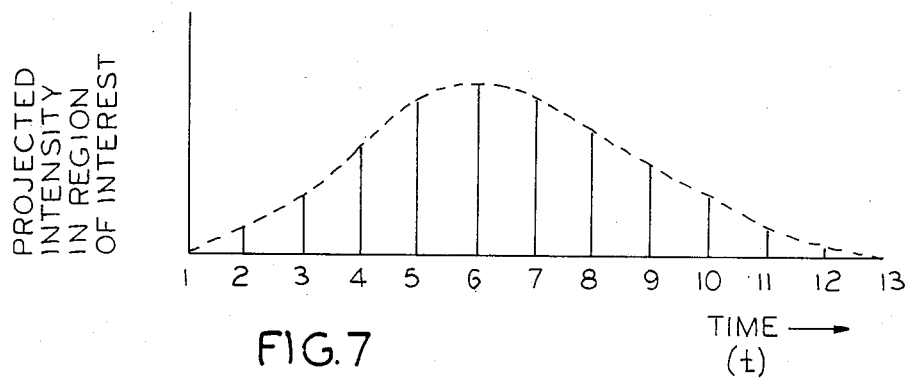
FIG. 7 is a diagram of the projected intensity of the contrast medium bolus versus time for the patient, for example, from which the images depicted in FIG. 6 were obtained.

Now one method of determining what the different matched filter multiplier values as a function of time should be will be discussed. Generally, a matched filter function can be determined and used to emphasize the projected intensity of the contrast medium bolus for every image frame. FIG. 7 shows a plot of the projected intensity of the contrast medium bolus versus time for a vessel in the region of interest. Most plots for projected intensity or contrast medium concentration versus time have this general shape. This bolus plot may be treated as being isolated from FIG. 1. The matched filter function $h_i(t)$ is typified in FIG. 8 and relates to the bolus or contast medium intensity plot of FIG. 7. Thus, any image obtained at any time, t, during the imaging sequence after the contrast medium bolus arrives in the region of interest will be weighted by the value of the ordinate, $h_i$, corresponding to the same time in the filter function plot. As stated earlier, to have a filter function sequence that has a dc component equal to zero is equivalent to requiring that the filter function values at the various times during the exposure sequence add up to zero. The filter function in FIG. 8 can be initially matched to the bolus and then modified to ensure that the sum of the filter functions is zero ($\Sigma h_i(t) = 0$).

Figure 8:
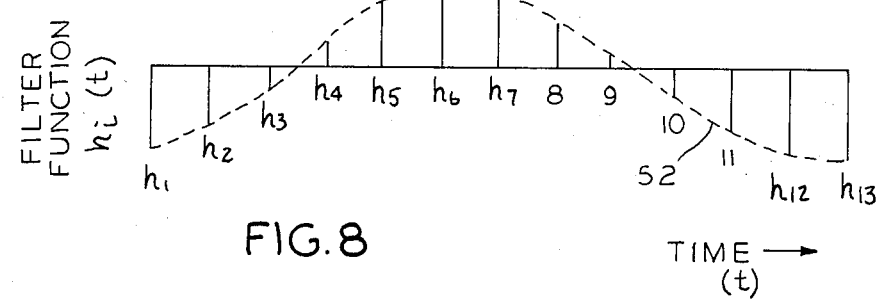
FIG. 8 shows the result of applying the unique filter function to the difference images obtained from the patient to whom FIGS. 6 and 7 relates.

It if were not for the fact that the sum of $h_i(t)$ must equal zero to eliminate all background and constant information from the images, a filter function which is above the abscissa or all positive in FIG. 8 would be satisfactory. However, the pre-contrast, post-contrast and after post-contrast images all have the same background due to soft tissue and bone and noise from the mask exposure for instance. The bolus function per se in FIG. 8 is always larger than zero, so the sum of values cannot equal zero. To get around this situation, negative-going functions such as those embraced within the curved dashed lines 51 and 52 are used. Negative curves 51 and 52 span over the time before and after bolus arrival and departure or, in other words, the time when no bolus is present but the background is present. The area above the abscissa in FIG. 8 is substantially equal to the sum of the two areas below the abscissa. In effect, it is just as if the curve in FIG. 7 were shifted downwardly to achieve the position in FIG. 8 although it should be recognized that the filter function of FIG. 8 is going to be applied to pre-contrast, post-contrast and after-post-contrast image signals.

On first impression it would appear that the negative values of the function h under the curves 51 and 52 which together have an area substantially equal to the area of the curve above the abscissa in FIG. 8 would bring about cancellation of all signals. This does not happen. The reason is that there is little or no x-ray contrast medium in the image representing signals when the filter function is negative. In effect when a h(t) is negative it is generally being applied to an image that has little or no contrast medium. Positive filter values generally weight images which contain a substantial amount of contrast medium.

The filter function values h(t) applicable to the respective image frames can be determined in various ways. Bolus projected intensity versus time plots for a particular blood vessel in a variety of patients may be obtained and averaged to derive a generally applicable plot of filter function values versus time. However, the time for the contrast medium concentration in a vessel to go from zero to maximum and back to zero concentration or projected intensity varies between patients and even between different blood vessels in the same patient. Thus, the method of determining the filter function values for each image frame that is preferred herein is to derive the information from difference images acquired from the patient presently being examined.

Figure 6:
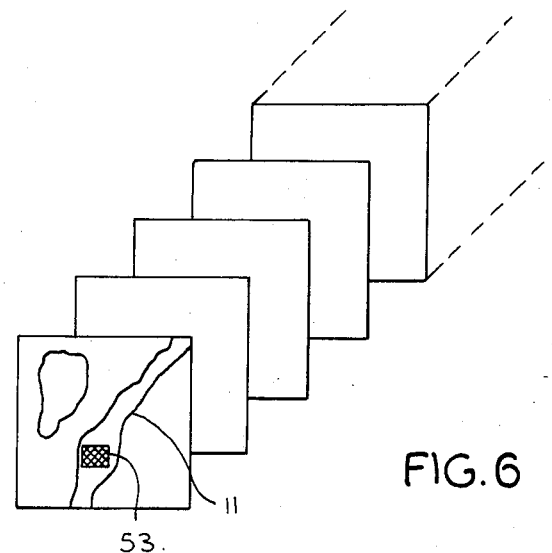
FIG. 6 is a diagram for explaining a preferred method of obtaining the filter function values by using projected intensity values of the contrast medium bolus that are unique to the patient being examined.

As discussed earlier the alternating sequence of low and high energy temporally subtracted images has been stored on disk 26 in readiness for performing the hybrid subtraction and matched filtering procedure which is now assumed to be necessary to reduce noise and suppress motion artifacts. Contrast medium will be present in some of the stored temporal difference images. An area or region of interest (ROI) of about 100 pixels square can be selected in a blood vessel zone that is representative of the projected intensity of the contrast medium during every image frame. This is shown diagrammatically in FIG. 6 where a sequence of 1 to N low energy temporal difference image frames are symbolized. The blood vessel is marked 11. The chosen ROI zone is shaded and marked 53. Projected intensity of the contrast medium in the ROI will go from zero to maximum and back to zero through the sequence of post-contrast images between 1 and N. The projected intensity values will vary in correspondence with the filter function values versus time in terms of TV frames or images. Thus, the filter function value for any difference image frame in the exposure sequence can be determined.

The hardware operations for obtaining the matched filter function values will be discussed in reference to FIG. 9. The low energy temporal difference image frames are stored in analog video signal form on disk 26. To start the filter function determining procedure, the low energy difference images are accessed from disk storage 26 and reviewed visually. This involves digitizing a difference image frame using ADC 46 and transferring the image directly to one of the digital frame memories 70. The transfer path is from the output of ADC 46 through buses 47 and 61, multiplier (MULT) 63, bus 67, arithmetic logic unit (ALU) 68 and bus 69 to frame memory 70. Of course, MULT 63 and ALU 68 are set to not act on the data during the transfer in which case anything that appears on their inputs comes out identically on their outputs. The contents of memory 70 are read out and passed through a MULT 84 and an ALU 83 without change. From the output of ALU 83 the digital image data goes through bus 86, MUX 40, gain and offset insertion circuit 42 and to DAC 43 for conversion to analog video signals. These signals drive TV monitor 36 and cause the difference images to be displayed on its screen 37 for review of one after another when desired.

Digressing momentarily, the timing and data transfer and manipulation functions for the FIG. 9 system are controlled by a computer system represented by the block marked 54. The external bus for the computer system is marked 55 and couples the computer to various electronic components of the system for control purposes. An operator's control and display terminal 56 is linked to computer 54. The terminal has a keyboard 57. The system software provides for the operator to produce a movable cursor on TV display screen 37 to designate the ROI by using a control on keyboard 57. A sequence controller 90, coupled to computer bus 55 and having other buses 91, 92 and 93, among other duties, controls transfer of images to and from disk storage 26 and frame memory 70.

Now continuing with determination of the filter coefficient values, the aforesaid difference images are displayed in sequence until a post-contrast image appears in which the contrast medium filled vessel has peak opacity. In this view, the operator sets the cursor on the ROI in the peak opacity zone. The computer is then provided with the location of the ROI zone. The sequence controller 90 then controls digitization of the entire sequence of stored difference images and the contents or pixel intensities in the ROI are sent from each image in frame memory 70 to computer 54 by way of its bus system 55. The computer is programmed to relate the intensities of the pixels in the ROI in each image to the number of the image or to the TV frame time in the sequence and thereby determine the bolus curve. The ordinates of the curve, of course, represent the values or matched filter coefficients of the difference images to which they pertain.

It should be mentioned that the difference image frames are given serial numbers such as 0 through 50 or whatever the highest number in the sequence is. This allows the operator to make positive identification of the peak contrast intensity frame. This frame number is inputted to the computer by way of keyboard 57 of the operator's terminal for the computer to match the filter function later with the stored image data as will be described.

Figure 4:
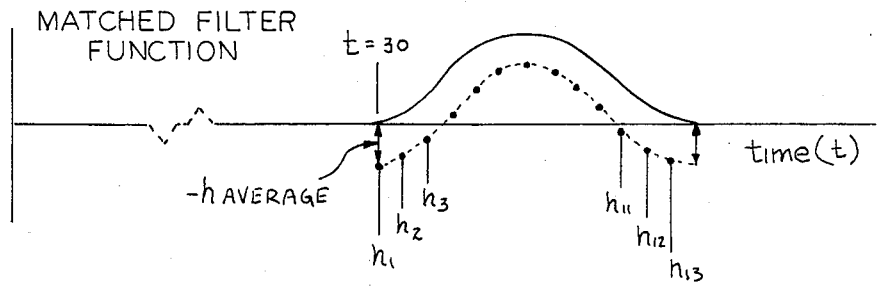
FIG. 4 shows a solid line plot of projected intensity of the x-ray contrast medium bolus in the blood vessel versus time and shows a dashed line plot of the matched filter function derived from the bolus intensity plot.

The matched filter function determining process is discussed further in reference to FIG. 4. Here the pre-contrast image sequence runs from t=0 to t=30 as an illustration. Contrast medium arrives at t=30 difference image frames. The projected bolus plot for the intensities within the sampling zone is shown as a solid line above the abscissa. Essentially the computer now has the data for plotting the bolus curve h(t) based on projected intensity versus difference image frame time. The computer is programmed to calculate the area under the solid line curve to get the average intensity so the solid line curve could be shifted down on the coordinates to form the dashed line curve wherein the sum of the negative areas below the abscissa is equal to the area of the dashed line function plot above the abscissa. Thus the sequence of coefficient values or matched filter function by which the frame data will be multiplied are the negative and positive values of the function related to the respective frames during which the filter function was derived.

Figure 15:
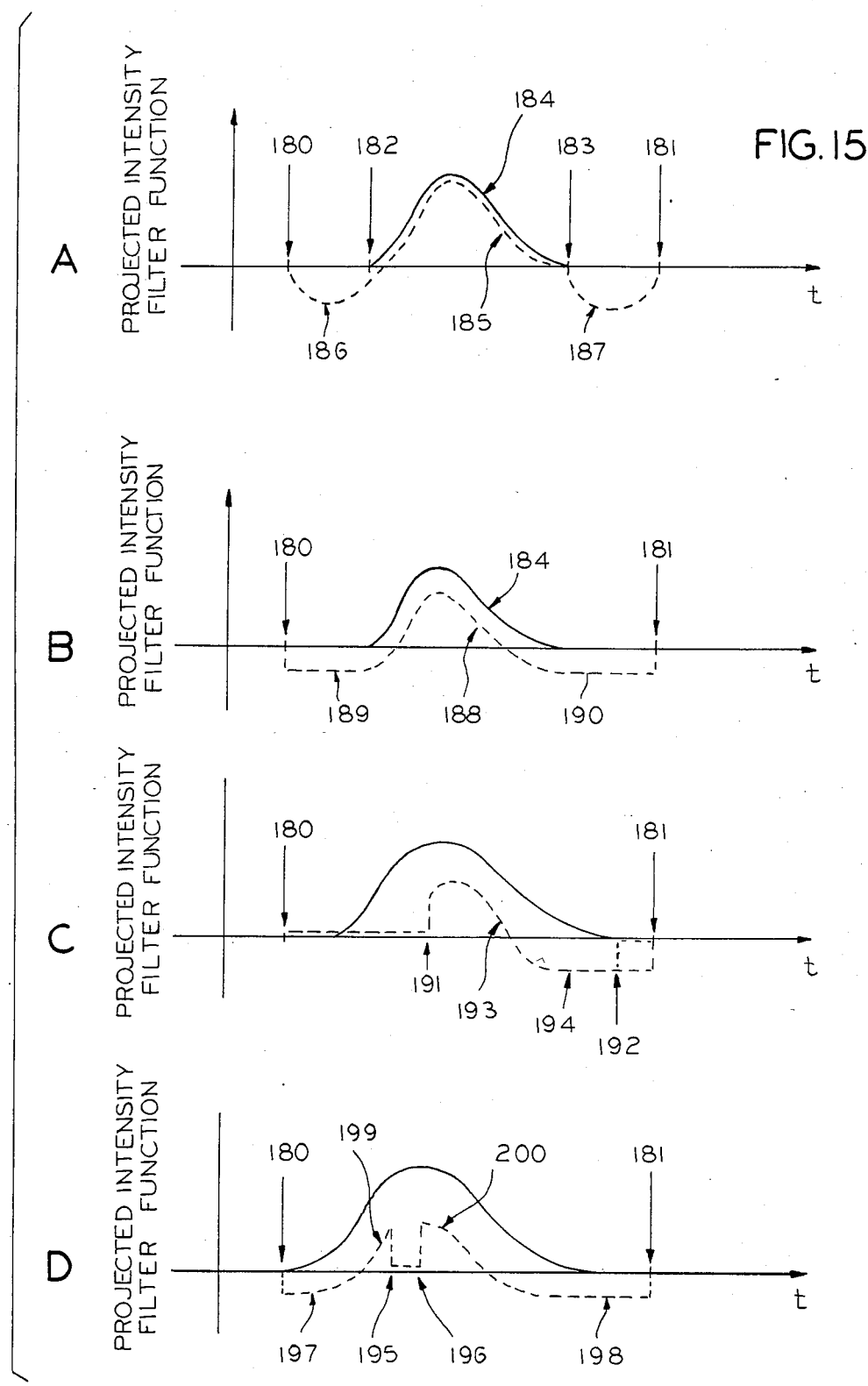
FIG. 15, comprised of parts A, B, C and D, shows specific types of matched filter functions.

In FIG. 15 several variations of matched filter functions are shown. These pertain first to several ways of forcing the dc frequency response to be zero; and second, to compensation for motion. This will now be demonstrated.

In FIG. 15A, the time (t) marked 180 is the first x-ray exposure in the total sequence and the time marked 181 represents the last exposure in the total sequence. The time marked 182 corresponds to the time of contrast medium arrival and the time at 183 corresponds to apparent full departure of the constant medium from the vessel of interest. Curve 184 is the measured projected intensity or opacification of the bolus while in the vessel of interest. Also in FIG. 15A is the dashed curve 185 which corresponds to a matched filter formed from the measured bolus. Note that it is proportional to the bolus itself during the interval between contrast medium arrival 182 and apparent departure 183. For exposure times preceding arrival and following apparent departure of the medium the filter function is assigned negative values as indicated by the dashed-line curves marked 186 and 187. This is done to insure that the integral of the matched filter over the entire exposure sequence from times 180 to 181 is equal to zero. if the exposure sequence were terminated at time marked 183 or prior to that time, there would be no area 187 but then area 186 would be enlarged to bring about an integral of the entire plot equal to zero. Similarly, if the first x-ray exposure occurred at time 182 or even after arrival of the constant medium, then curve 186 would not be present and curve 187 would be enlarged to obtain an integral equal to zero. This is the general case of a matched filter.

Formation of a specific type of matched filter which can occur in practice is shown in FIG. 15B. Here the exposure sequence is again started at time 180 and terminated at 181 as in FIG. 15A. Here though, the matched filter function 188 is formed by subtracting the average value of the bolus curve 184 from all points in time between the times marked 180 and 181. This in effect amounts to shifting bolus curve 184 down so that the areas of the negative portions 189 and 190 add up to an area equal to the positive area in which the total integral again equals zero.

Another specific type of matched filter which can occur in practice is shown in FIG. 15C. The exposure sequence again begins at a time marked 180 and terminates at time marked 181. Sometimes not all images in the sequence are in registration because, for instance, the patient has moved. For example, in FIG. 15C, movement is assumed to have occured prior to the time at 191 and again after time marked 192. Thus, the matched filter values should only be formed between times when there is registration such as between times marked 191 and 192. Here again the positive part 193 area is equal to the negative part 194 area so the total integral equals zero as is required for cancellation of static image features. Filter function values are set equal to zero for times outside of the integral used preceding time marked 191 and following time marked 192.

FIG. 15D is another specific matched filter that can occur in practice. Here patient motion has occurred between times marked 195 and 196. The images at all other times happen to be in registration. Now the filter function values between times marked 195 and 196 are made equal to zero since the images made during movement are cast out. Using all other times and images, negative filter function values 197 and 198 are formed and their total negative area is equal to the positive dashed line parts 199 and 200 so the total integral is equal to zero as in the preceding examples.

In a rigorous mathematical sense the matched filter curves 189-188-190 of FIG. 15B is not exactly proportional to the observed or estimated bolus curve 184. This is because the matched filter coefficient values have been slightly modified; e.g. the filter was shifted downward to insure that the integral of the filter is zero. Similarly, in FIGS. 15C and D the proportionality does not rigorously hold because filter coefficient values have been set equal to zero for those images which are being discarded. Nevertheless, since the overall shape of the matched filter function is generally similar to to shape of the bolus curve the matched filter function is said to be substantially in proportion to the bolus curve.

In combining energy subtraction and temporal subtraction as required for hybrid subtraction, the low energy temporal difference image frames and high energy temporal difference image frames are consecutively multiplied by the matched filter coefficients pertaining to the respective frames. Referring to FIG. 9, after the filter functions are calculated they are loaded into coefficient storage devices 59 and 60. These devices are basically digital memories in which the matched filter coefficients are at locations whose addresses correspond to the numerical sequence of the low and high temporal difference images $T_{1,L}$ to $TD_{N,L}$ and $TD_{1,H}$ to $TD_{N,H}$.

The matched filtering and hybrid subtraction process proceeds after the addressable coefficient storage devices are loaded. The low and high energy temporal difference images are then read off of disk 26 in order and digitized in ADC 46. In the low energy channel, by way of a bus 61 the low energy temporal difference image frames become one input to a multiplier (MULT) 63. The other input 65 to MULT 63 provides the respective filter points or coefficient sequence from storage device 59. By way of bus 62 the high energy temporal difference image frames become one input to a MULT 64 and its other input 66 provides the filter function from storage device 60.

The output bus 67 from MULT 63 is an input to an arithmetic logic unit (ALU) 68. The output bus 69 from ALU 68 is an input to the full frame digital memory 70. The output bus 71 feeds back by way of a bus 72 and becomes another input to ALU 68.

The high energy channel is similar. The output bus 74 from MULT 64 is one input to an ALU 75. Its output 76 is input to frame memory 77 whose output 78 feeds back by way of a bus 79 to the other input 80 of ALU 75.

What happens in the two channels between temporal difference image inputs to MULTS 63 and 64 and the outputs 71 and 78 of frame memories 70 and 77 will now be discussed in detail. The sequence controller 90 has address buses 91 and 92 for addressing the coefficient storage devices 59 and 60. The controller 90 has a line 93 for synchronizing readout of the low and high energy temporal difference images from disk 26. When a low energy temporal difference image frame is read out, the sequence controller addresses the storage device 59 so it puts out the corresponding matched filter coefficient to MULT 63 where it multiplies the digital data representing every pixel in the frame. When a high energy temporal difference image is read out, the sequence controll addresses storage device 60 to insert the corresponding filter coefficient into MULT 64 for multiplication. The first high and low energy temporal difference images in a sequence simply pass through ALUs 66 and 75 and go into memories 70 and 77. Subsequent temporal difference images after having been multiplied by their filter coefficient are then added in ALUs 68 and 75 to the fed back contents of the respective frame memories 70 and 77. After having thus read out and processed the low and high energy sequences of images from disk 26, memory 70 will contain the term in parentheses within the first brackets of Eq. 2 and frame memory 77 wil contain the term in parentheses within the second brackets.

As indicated by Eq. 2, the terms in parentheses must still be multiplied by the weighting constants $k_L$ and $k_H$ before the terms in brackets are subtracted to yield the resulting hybrid or temporal and energy subtracted image in which soft tissue and bone are cancelled and only the x-ray contrast medium remains. MULTs 84 and 85 are provided for multiplying each matched filtered image pixel out of frame memories 70 and 71, by $k_L$ and $k_H$ respectively. After the multiplication the resulting images are input on buses 81 and 82 to ALU 83. These resulting images are represented by the contents of the first and second brackets in Eq. 2. In ALU 83, the second brackets are subtracted from the first brackets contents and the final hybrid subtracted image data is output from ALU 83 on bus 86. After being gated through MUX 40 the hybrid image data is operated on by gain and offset inserting circuit 42 and DAC 43 as previously explained and the image of the contrast medium filled vessel 11' is displayed on television screen 37.

In the mode just described, temporal subtraction was performed during image acquisition and energy subtraction and matched filtering were performed during reprocessing. In the next or second hybrid subtraction mode to be described in reference to FIG. 3, energy subtraction is performed first and then temporal subtraction and matched filtering are done concurrently.

Figure 3:
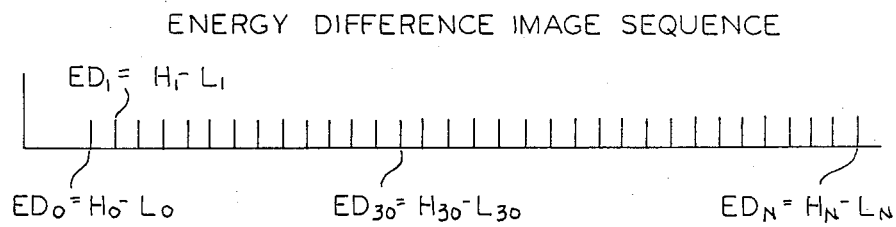
FIG. 3 is a diagram for explaining how in another mode energy difference images are acquired and stored on video disk and subjected to temporal subtraction and matched filtering retrospectively.

In the second mode, image acquisition is in the format of FIG. 1 as in the previously discussed mode. In other words, a sequence of alternating low and high x-ray energy pre-contrast, post-contrast and after post-contrast are made as before. However, in this second mode energy subtraction is done concurrently with image acquisition and in a reprocessing mode temporal subtraction is done in conjunction with matched filtering. Energy difference imaging is symbolized in FIG. 3 as previously indicated. It shows that when the first pair of low ($L_0$) and high ($H_0$) pre-contrast exposures are made as in FIG. 1, $L_0$ is subtracted from $H_0$ to produce an energy difference image ($ED_0$) which is labeled $ED_0 = H_0 - L_0$ in FIG. 3. Similarly, the low and high energy frames in each successive pair throughout the exposure sequence are subtracted to produce a series of energy difference image frames. Typically, about 80 low and high energy exposures may be made so 40 difference images ranging from $ED_0$ to $ED_N$ in FIG. 3 are made. In actual practice, before the low and high energy frames in a pair are subtracted, all of the pixels comprising a low energy frame are multiplied by a weighting factor ($k_L$) and the pixels in the high energy frame are multiplied by a different weighting factor ($k_H$). The values of $k_L$ and $k_H$ are the same as discussed before. So each energy difference frame is $ED_M = k_L L_M - k_H H_M$ where $0 \leq M \leq N$. The values of the weighting constants $k_L$ and $k_M$ are such that when the frames are subtracted, soft tissue will cancel out and the difference images, $ED_M$, will only contain bone if the pair is a pre-contrast or other post-contrast pair and will only contain bone and x-ray contrast medium in the blood vessel if the pair is a post-contrast pair.

Figure 10:
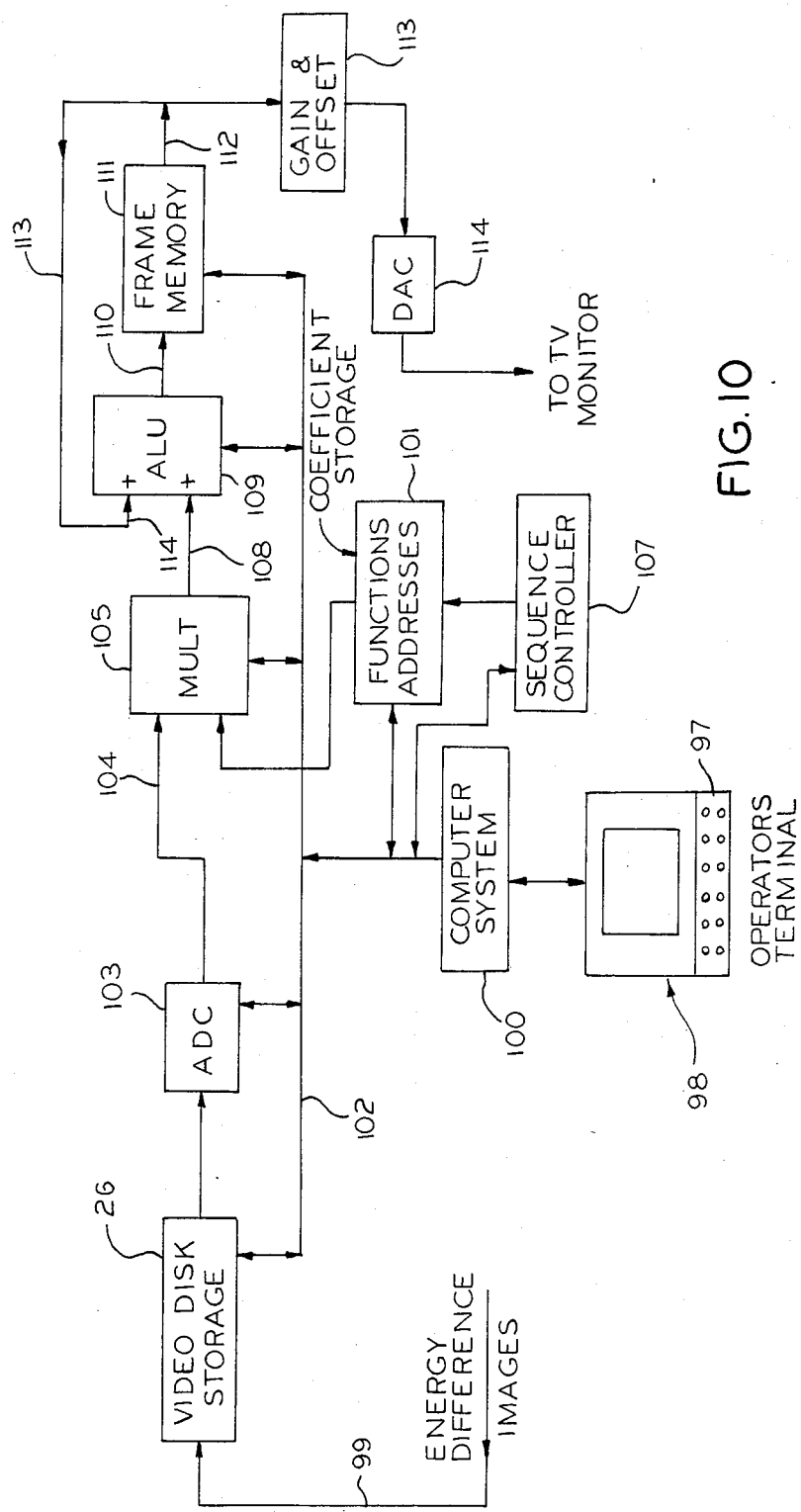
FIG. 10 is a simplified diagram of a system for conducting another of the matched filtering hybrid subtraction methods.

A simplified system showing only what is required for doing energy subtraction first and temporal subtraction and matched filtering later is depicted in FIG. 10. The video disk storage is marked 26 again. Assume that the logarithmically expressed image frames have been weighted and subtracted in a video processor such as the one marked 22 in FIG. 9 and that the series of energy difference images, $ED_0$ to $ED_N$ are fed into disk 26 by way of bus 99 and are in analog video signal form. Then the combination matched filtering and temporal subtraction operation can proceed.

The first step is to obtain the matched filter function values for the respective energy difference image frames and load them into coefficient storage device 101 in FIG. 10 as was done in the previously described mode. As in the previous case, every analog video image frame is converted to digital values in ADC 103 and transferred directly to frame memory 111. MULT 105 and ALU 109 are set to not act on the data during this transfer. From the output of frame memory 111 the digitized image frame data goes through the gain and offset insertion circuit 113 and DAC 114 for conversion to analog video signals for enabling display of the energy difference images, one after another, on the TV monitor.

The timing and data manipulation functions in the FIG. 10 system are controlled by a computer system 100 associated with an operator's display and control terminal 98 which has a keyboard 97. The computer external bus is marked 102. A sequence controller 107 controls, among other things, transfer of difference image data to and from disk storage 26 and frame memory 111.

To obtain the filter coefficient values, $h_i$, the energy difference images are displayed in sequence on the TV monitor until a post-contrast image appears that has peak opacity in the contrast medium filled vessel. The computer software provides for the operator to set a cursor on the TV screen in the peak opacity region of interest (ROI). Computer 100 is then provided with the ROI zone location. Sequence controller 107 then controls digitization of all stored energy difference images and the pixel intensities or brightness level in the same ROI of each image in frame memory 111 are sent to the computer by way of bus system 102. The computer is programmed to relate the intensities of the pixels in the ROI in each image or TV frame time in the sequence and thereby determine the bolus curve. The ordinates of the curve represent the values or matched filter coefficients, $h_i$, of the energy difference images to which they pertain. The ordinates of the curve must then be modified to have an average value of zero as was previously described in reference to FIGS. 4 and 8. The matched filter coefficients are then loaded into coefficient storage device 101 at addresses corresponding to the respective image frame numbers to which they pertain.

Now for the matched filtering process the energy difference image frames can be read off of analog video disk 26 in sequence. As the frames come off they are converted to digital pixel values in ADC 103 and conducted to one input 104 of a multiplier (MULT) 105. Another input to MULT 105 is marked 106. This input is for the matched filter function coefficients. The sequence controller 107 is clocked by the computer. As the energy difference frames are inputted in consecutive order to input 104 of MULT 105, the controller 107 addresses the coefficient generator with the frame number and causes it to supply the coefficient to input 106 of the MULT that pertains to the image frame that is being entered through input 104. Thus, in this mode every energy difference frame is multiplied by the appropriate matched filter value or coefficient. Recall that there are some negative as well as positive matched filter values as was previously explained in reference to FIG. 8 and FIG. 4 also.

After each energy difference frame has been multiplied by its corresponding matched filter function or coefficient, $h_i$, in MULT 105 it is fed to one input 108 of an ALU 109. The first energy difference image in the sequence simply goes by way of bus 110 to a full frame digital memory 111. Its output bus 112 connects by way of a bus 113 to the second input 114 of ALU 109. This arrangement provides for having ALU 109 add the present contents of frame memory 111 which are on its input 114 to the next frame that comes in on bus 108 for returning the result to frame memory 111. After the whole sequence of matched filtered difference images have been summed there is stored in frame memory 111 the digital data for a single final image which has not only been filtered but subjected to the equivalent of temporal subtraction as will be explained.

In FIG. 10 the final digital image data or signal has gain and offset applied to it in circuitry 113. After that the digital signal is converted to analog video signals in DAC 114 for driving the TV monitor and displaying the motion artifact free and improved signal-to-noise ratio image that results from the matched filtering and summation process.

Achieving the equivalent of temporal subtraction results from the fact that a matched filter is chosen that had a dc response equal to zero as was previously discussed in connection with FIG. 4 because the sum of the coefficients of the matched filter functions is made equal to zero. Thus, anything that remains stationary or constant from one energy difference image to the next is cancelled out. To summarize, soft tissue that may or may not have moved was cancelled out by energy subtraction and any bone which remained constant was cancelled out in the matched filtering and summation process. Cancelling out everything that is constant is what is achieved in temporal subtraction.

In what was described earlier as the first mode of hybrid subtraction, temporally subtracted low and high x-ray energy difference images were produced and stored alternately on disk. The subtractions of the low and high energy masks from each successive and alternate low and high energy x-ray exposure over the whole exposure sequence were made contemporaneously with image acquisition and stored. Then the data for the successive low and high energy temporal difference images were match filtered separately, weighted and lastly subjected to energy subtraction to yield the final hybrid subtraction image. Thus, temporal subtraction was done first, matched filtering next and finally energy subtraction was done.

The order of events recited in the preceding paragraph can be changed. That is, energy subtraction can be done before matched filtering. In this case the temporally subtracted low and high energy difference images are stored on disk 26 during acquisition as in the preceding case. But in this case, the digitally represented low and high energy temporal difference images are weighted by multiplying them by $k_L$ and $k_H$ in the equivalents of MULTs 84 and 85 in FIG. 9 as the difference images are being accessed from disk 26. For example, the first pre-contrast low energy temporal difference image in the sequence is accessed from disk 26 and directly weighted or multiplied by $k_L$ as in MULT 84 and simultaneously the first pre-contrast high energy temporal difference image is directly weighted or multiplied by $k_H$. The simultaneously weighted low and high images are then subtracted from each other such as by ALU 83 to produce a pre-contrast hybrid image which is to be matched filtered. All of the low and high stored temporal difference images are similarly weighted in succession, that is by going through the entire pre-contrast, post-contrast and after-post-contrast sequence so that a whole sequence of hybrid subtraction frames are generated in succession. Every time a hybrid image frame is generated, however, it is multiplied immediately by the matched filter coefficient that applies to that frame. In this case, only one of the coefficient storage devices 59 or 60 is required. Assume that the matched filter coefficients have been computed as previously described and that they are in one coefficient storage device such as 59 for example. In this case, when each hybrid image frame is formed and is output from the equivalent of ALU 83 for example, the image frame data is sent directly to one of the inputs 61 of MULT 63 whose other input 65 is the matched filter coefficient for that frame. After multiplication by the matched filter coefficients in ALU 63, the frames are summed in the accumulator comprised of ALU 68 and frame memory 70 as in the previously described modes where matched filtering was done before the hybrid images were formed. In the case now being described, when the summation for all of the individual hybrid frames in the exposure sequence is done, a single matched filtered hybrid image resides in frame memory 70 or its equivalent. This image can be transmitted through digital MULT 84 and ALU 83, while they are held in a state wherein they do not affect the data, and to the television monitor 36 for display and also to memory 87 for storage. It is to be noted, that for the sake of brevity, the bus is not shown in FIG. 9 which would be used to transfer the succession of unfiltered hybrid image frames from the output of ALU 83 to the one input 61 of the MULT 63 wherein they are multiplied by the filter coefficients before summation.

In all previously described modes of operation, the temporally or energy subtracted images were put in disk storage 26 after subtraction in video processor 22. It is also contemplated to store the low and high energy images prior to subtraction on disk 26. For instance, the images obtained by alternate low and high energy x-ray exposures as in FIG. 1 can go directly to disk as raw data. Having the raw unsubtracted image data retained in storage affords an opportunity to process the data in various ways before it undergoes subtraction or matched filtering. Thus, the data are always available for as long as is required to perform any of the described matched filtering and other signal processing or preprocessing as well.

Now to be described is a matched filtering scheme that employs integration processes to acquire a series of alternating low and high temporally subtracted images for storage on disk, or a series of energy subtracted to be stored on disk, or a series of alternating low and high energy images which are not subtracted but stored on disk for subtraction and matched filtering later. The integration processes can improve signal-to-noise ratio.

A temporal integration process is characterized by integrating several successive low energy exposure images and several high energy exposure images to form low and high energy mask images. Then integrate equal numbers of successive low energy exposure images and high energy exposure images and at the end of each integration interval subtract the low energy integrated mask image from the present integrated low energy image and store the difference image on disk and, alternatingly, subtract the high energy exposure mask image from the present integrated high energy image and store the difference image on disk. Thus, when an exposure sequence is completed there will be a series of low energy integrated temporal difference images alternated with high energy integrated temporal difference images on disk for subsequent matched filtering and energy subtraction.

The temporal integration process can be performed in video processor 23 which has several frame memories, not shown. Four memories are used for present purposes. The number of low and high energy exposures to be integrated will typically be three to five. Typically the exposures may be made at a rate of about five per second. Assume, for example, that groups of four exposures are to be integrated. As in all cases, the analog video signals for each exposure coming out of TV camera 17 are digitized in ADC 19 and converted to logarithmic form in Log LUT 21 and sent to video processor 22. The first four low energy images ($L_0$ to $L_3$) in FIG. 1, for instance, would be integrated in a first memory in the video processor 22 and stored there as the low energy exposure mask image. The interleaved or alternating first four high energy exposure images would be integrated in a second memory in the video processor and stored as the high energy exposure mask image. Every one of the next groups of four low energy images would be integrated in a third memory in the processor and every one of the next group of four high energy images would be integrated in a fourth memory in the processor. At the end of each low energy image group integration, this low energy integrated image in the third memory has the low energy mask that is stored in the first memory subtracted form it and the resulting low energy temporally subtracted or difference image is sent to disk storage 26. At the end of each high energy group integration, this integrated image in the fourth memory has the low energy mask in the second memory subtracted from it and the resulting high energy temporally subtracted image is sent to disk storage 26. The process of subtracting the integrated mask images from the integrated groups is repeated for the entire exposure sequence to obtain the series of alternating low and high temporal difference images on disk.

An energy exposure integration process can also be used to improve signal-to-noise ratio. In this case, a group of several low energy exposure images are integrated in a first processor memory while several interleaved high energy exposure images are integrated in a second processor memory. The integrated low energy exposure images are subtracted from the integrated high energy images and each resulting energy difference image is stored on disk. Alternate groups can be integrated in third and fourth memories to avoid overlap or loss of image data.

Another feature of the invention is to perform filtered hybrid subtraction in a recursive mode as an alternative to direct matched filtering.

Basically, in recursive filtering a sequence of low and high energy exposure pairs are made. However, from the beginning of the sequence to the end, every time there is a low energy and a high energy exposure pair formed, the low energy image, $I_L$, is immediately multiplied by a weighting factor, $k_L$, and the associated high energy image $I_H$ is multiplied by a weighting factor, $k_H$. After that, the resulting images are subtracted from each other to produce a sequence of energy difference images, ED. Thus, each $ED = k_L I_L - k_H I_H$. As explained earlier this weighting and subtraction of the different energy images results in cancellation of soft tissue in the respective difference images ED.

As the sequence of energy difference images are produced they are fed simultaneously to individual recursive filter channels that are characterized by having different time constants. Each of the filter channels has a dc response of 1 which means that there is no cancellation of information that is constant in the succession of pre-contrast, post-contrast and after post-contrast images. However, in accordance with the invention, the summations of the recursively filtered images which are output from the two channels are finally subtracted from each other whereupon the dc response becomes 1-1=0 to thereby cancel everything that is constant among all of the energy difference images and leaving only that which changes between pre-contrast and post-contrast exposures. It is only the x-ray contrast medium that is changed and that is what the physician hopes to be able to visualize with minimum or no obscuring background.

Figure 11:
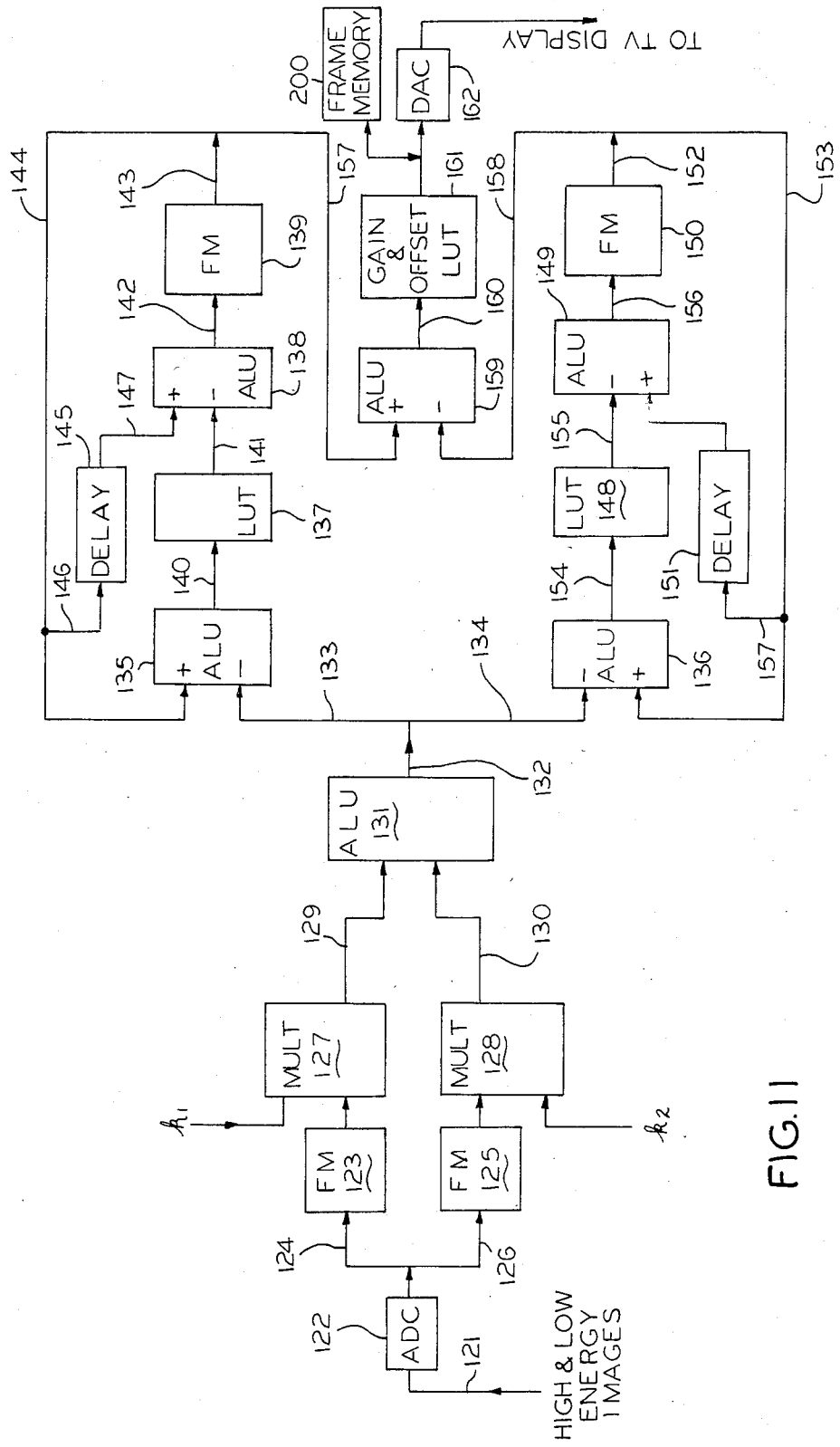
FIG. 11 is a diagram of hardware for performing hybrid subtraction by recursive filtering.

Suitable hardware is shown in FIG. 11 for performing hybrid subtraction by doing energy subtractions to cancel soft tissue and doing recursive filtering to achieve the equivalent of temporal subtraction, that is, to cancel noise and everything that is constant in the x-ray exposure sequence.

Assume in FIG. 11 that high and low energy video images are coming out of TV camera and are input on bus 121 to an ADC 122. The low energy image in a pair is switched into frame memory (FM) 123 by way of bus 124. The ensuing high energy image is switched into FM 125 by way of bus 126. In a MULT 127, the pixels comprising the low energy image frame are multiplied by a weighting factor $k_1$ as indicated. In MULT 128, the high energy frame is multiplied by a weighting factor $k_2$. The weighting factors have values that result in soft tissue being cancelled when the high and low energy images are subtracted as previously explained. The low and high energy images are transferred by way of buses 129 and 130 to ALU 131 where the weighted energy subtractions occur. Thus, the output on bus 132 from ALU 131 is a series of pre-contrast, post-contrast and after-post-contrast energy difference images, Ed. An equation for the output on bus 132 is:

$$ED = k_1 I_L - k_2 I_H \quad \text{(Eq. 2)}$$

where $I_L$ and $I_H$ are the individual low and high energy images in the sequence.

The energy difference images, ED, are simultaneously fed into two recursive filter channels by way of branch buses 133 and 134. The recursive filters have different time constants. The input stage for the first channel is an ALU 135 and for the second channel is an ALU 136. The first channel is comprised of ALU 135, a look-up table (LUT) 137, an ALU 138 and a full frame digital memory (FM) 139. The components are connected by way of buses 140, 141 and 142. The output bus 143 from FM 139 is coupled by way of a feedback bus 144 to input stage ALU 135. A delay circuit 145 is coupled between feedback bus 144 and one input of ALU 138 by means of buses 146 and 147 for reasons that will be explained.

The second recursive filter channel is structurally the same as the first channel. The second channel is comprised of ALU 136, LUT 148, ALU 149, FM 150 and a delay circuit 151. Output bus 152 from FM 150 is coupled by way of a feedback bus 153 to one input of ALU 136. Other interconnecting buses are marked 154–158.

In recursive filtering, as previously indicated, the digitized energy subtracted images, ED, are fed into each channel simultaneously. The purpose of full frame memories 139 and 150 is to permit all previous image frames to be added to the presently incoming difference image frame ED such that the relative importance of a signal on frames previous is determined by the value of a coefficient "K". For example, if K were equal to 0.5 and $(1-K)$ were equal to 0.5, the output signal from the frame memory would consist of ½ of the present frame signal, ¼ of the next earlier frame signal, ⅛ of the next earlier frame, 1/16 of the next frame and so on such that any frame preceding the present signal has little weight in the summation of signals or image frames. When a multiplicity of frame signals acted upon by the selected constants are summed, the result is a signal identical to any one of the summed signals and of the same magnitude of the unattenuated incoming present difference image signal because the sum of K and $(1-K)$ is always unity. It can be demonstrated that the improvement in signal-to-noise ratio is equal to $10 \log (2-K)/K$ decibels.

Figure 12:
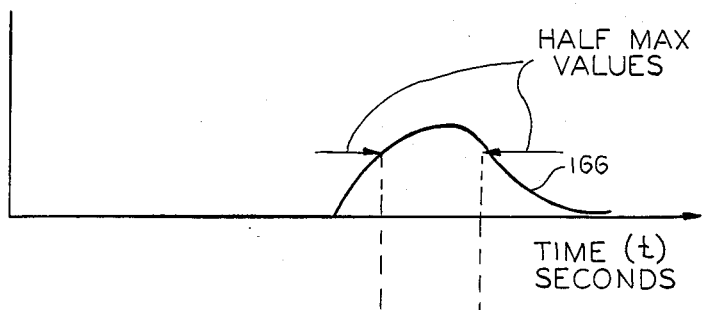
FIGS. 12, 13 and 14 are for facilitating discussion of the recursive filter mode.

The foregoing basic recursive filtering process is to be carried out in the FIG. 11 channels and the constant K will be used in one channel and a different constant K' will be used in the other channel. The results of the summations of the sequence of difference images that are output from FM 143 and FM 150 will be subtracted, whereby, in accordance with the invention, everything that is constant in the successive images will be cancelled out but the x-ray contrast medium outlining the vessel will remain. This is equivalent to the temporal subtraction step which is required for hybrid subtraction. The matter of choosing the different constants K and K' will be discussed in reference to FIGS. 12–14. In FIG. 12 the sequence of low and high energy exposures occur along the time axis as was the case in FIG. 1. The contrast medium bolus 166 comes and goes during the indicated time interval. The two half-maximum projected image intensity points are indicated. The time between half-maximum intensities is of primary importance.

Figure 13:
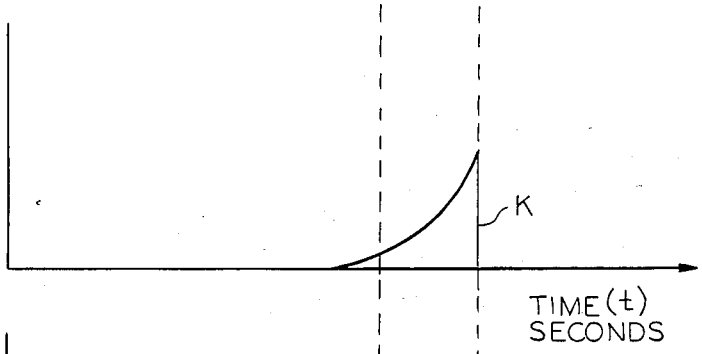
Figure 14:
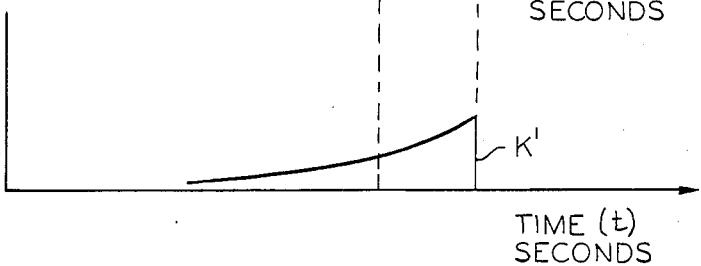

FIGS. 13 and 14 show the time-reversed impulse response functions for the respective recursive filter channels. The impulse response is demonstrated by inserting only one image into the channel and observing how the signal value in the frame memory is reduced as it is repeatedly operated on by $(1-K)$. In FIG. 13 the value of K would be higher than the value of K'. The higher valued constant K results in the shorter accumulating time as in FIG. 13 and the lower value constant results in the longer accumulating time as in FIG. 14. In FIG. 13 the pre-contrast signals have little weight and in FIG. 14 they have substantial weight.

The recursive filtering process in one channel may be expressed as follows:

$$S_n = KED_n + (1-K)S_{n-1} \quad \text{(Eq. 3)}$$

The right side of this equation requires that any incoming energy difference image $ED_n$ be multiplied by the constant K and that the present sum of the images in FM 139, that is, $S_{n-1}$ be multiplied by $(1-K)$ and added to the first term to produce the sum of the filtered images, $S_n$, at the end of the sequence. The preceding equation can be rewritten as follows to facilitate execution in the particular circuit element arrangement in FIG. 11:

$$S_n = S_{n-1} - K(S_{n-1} - ED_n) \quad \text{(Eq. 4)}$$

Consider that K is used in the uppermost channel in FIG. 11 and that it has a higher value than K' and this produces the shorter time constant or accumulating time in conformity with FIG. 13.

The equation for the lowermost recursive filter channel in FIG. 11 is:

$$S'_n = S_{n-1} - K'(S_{n-1} - ED_n) \quad \text{(Eq. 5)}$$

which has the same form as the preceding equation but a lower value constant, K'. The lower constant results in the longer time constant or accumulating time in conformity with FIG. 14.

In FIG. 11, the successive energy difference images Ed are input by way of bus 133 to ALU 135. The other input of ALU 135 gets the feedback by way of bus 144 of the contents of the FM 139 which is the sum of the images preceding the latest one or, in other words, $S_{n-1}$. The output of ALU 140 is thus $(S_{n-1} - ED_n)$ on bus 140. These successive values are an address to LUT 137 which contains K and simply multiplies K times the value in the last mentioned parentheses. Thus, the output of LUT 137 on bus 141 is:

$$K(S_{n-1} - ED_n) \quad \text{(Eq. 6)}$$

The process of feeding $S_{n-1}$ into ALU 135 and LUT 137 takes a finite amount of time such as the time to clock a few pixels. It is necessary to combine the preceding equation 5 from $S_{n-1}$ to produce $S_n$ in ALU 138. So $S_{n-1}$ is always fed from bus 144 to the + input of ALU 138 through delay circuit 145 to make up for the time used by ALU 135 and LUT 137. In any event, the output of ALU 138 on bus 142 is $S_n$ and this is returned to FM 139 for as many times as there are energy difference images, ED, in the exposure sequence.

The lowermost recursive filter channel in FIG. 11 that begins with ALU 136 and ends with FM 150 operates similarly to the channel just described although LUT 148 contains the long time constant K'. The final summation image $S'_n$ is completed in FM 150 at the same time as $S_n$ is completed in FM 139.

The final step is to feed the summation images from FM 139 and FM 150 by way of buses 157 and 158 to alternate inputs of an ALU 159 wherein the images are subtracted to produce a final hybrid video image frame on the ALU output bus 160. The digitized pixels comprising the final hybrid video image are fed to an LUT 161 wherein gain is applied for filling the dynamic range of the television display and offset is inserted to obtain the proper gray scale. The LUT 161 feeds the digital-to-analog converter (DAC) 162 wherein the digital frame is converted to analog video signals for driving the TV monitor to thereby display the single final image that resulted from the x-ray exposure sequence.

Earlier it was explained that the dc components of the signals in the two recursive filters were unaffected by the filtering operations, because whatever remained at constant intensity in one channel remained constant in the other channel. The only variable was the contrast medium intensity. Thus, when the final subtraction takes place in ALU 159 the constant matters cancel and all that remains is the contrast medium image signal that defines the blood vessel.

I claim:

1. A method of imaging a blood vessel in a body where the period before a bolus of x-ray contrast medium arrives in the vessel is designated the pre-contrast period, the period during which contrast medium is flowing through the vessel is designated the post-contrast period and the period following the latter when the medium has left the vessel is designated the after-post-contrast period, and where an x-ray source, when energized, projects a beam through said body to produce x-ray images, and including means operative to produce data representative of the respective images, the method including the following steps:

initializing a sequence of pairs of low and high x-ray energy exposures of the blood vessel during the pre-contrast period and continuing the exposures at least into the post-contrast and optionally into the after post-contrast periods to thereby provide data representative of the respective images resulting from the exposures, the data representative of an image in a pair resulting from one pre-contrast exposure at said low x-ray energy being designated the low energy mask image data and the data representative of an image resulting from one pre-contrast exposure in said pair at said high x-ray energy being designated the high energy mask image data, after the low and high energy mask image data are acquired perform temporal subtraction constituting subtracting the low energy mask image data from the data for each of the ensuing low energy images and send the resulting series of low energy temporal difference images data to storage as they are produced and alternately subtracting the high energy mask image data from the data for each of the ensuing high energy images and send the resulting series of high energy temporal difference images data to storage as they are produced, said temporal subtraction causing data representative of structure that remains constant throughout the sequence of images to be cancelled and data representative of said contrast medium and data representative of structure that changes during said sequence remain, access from storage the low energy temporal difference images data in succession and the high energy temporal difference images data in succession and multiply said successive low energy temporal difference images data by matched filter coefficients, respectively, and multiply said successive high energy temporal images data by said matched filter coefficients, respectively, said matched filter coefficients by which said images data are multiplied being proportional to the projected intensity, (h), of the x-ray contrast medium at times (t) and registered in time with the post-contrast temporal difference images so that a selected one of the coefficients is applied to the corresponding post-contrast temporal difference image containing maximum contrast medium, and the coefficients applied to the pre-contrast temporal difference images and any after-post-contrast temporal difference images are selected so that the sum of all of the coefficients equals zero, multiply said low energy temporal difference images data by their respective matched filter coefficients and sum the results and multiply said high energy temporal difference images data by said coefficients, respectively, to thereby produce one set of data representative of a matched filtered low energy temporal difference image and another set of data representative of a matched filtered high energy temporal difference image, multiply said one low energy temporal difference image data set by a constant ($k_L$) and said other high energy temporal image data set by a constant ($k_H$), said constants being so chosen that when said sets of multiplied image data are subtracted data representative of motion of a specific material are substantially cancelled, and after the preceding multiplications, subtracting the resulting sets of data to yield a set of data representative of the image of the contrast medium in said blood vessel.

2. The method as in claim 1 wherein said coefficients are determined by measuring the projected intensity of the contrast medium at a zone in said vessel versus time over the period during which contrast medium is typically present in said vessel in one or more representative human bodies into which contrast medium has been injected for reaching the vessel corresponding to the vessel of interest in said body being examined, then using coefficients that are proportional to the intensity at any time to multiply the low energy temporal difference images data and the high energy temporal difference images data representing images acquired at a corresponding time in said body being examined.

3. The method as in claim 1 wherein said coefficients are determined by displaying in sequence the series of temporal difference image data that has been stored and selecting a corresponding zone in the sucessive post-contrast images obtained while said contrast medium was flowing in said vessel which zone is representative of the projected contrast medium intensity in the respective displayed temporal difference images, determining the intensities (h) at said zones in each of the post-contrast temporal difference images and converting said intensities (h) to match filter coefficients that are respectively proportional to intensities (h) at successive times (t) at which the temporal images were acquired, and storing said coefficients and accessing them in sequence for said multiplication of the accessed low energy temporal difference image data and said multiplication of the accessed high energy temporal difference image data.

4. The method as in claim 3 wherein the intensities (h) at said zones are determined in each of the post-contrast temporal difference images, intensities (h) of zero are assumed for the pre-contrast and after-post-contrast temporal difference images, if any, the average intensity ($\bar{h}$) of the entire set of measured or assumed intensities (h) is determined, and the matched filter coefficient at a time (t) is set proportional to the difference between the intensity (h) measured or assumed at that time (t) and the average intensity ($\bar{h}$).

5. The method as in any one of claims 1, 2, 3, or 4 wherein said coefficients applied to the respective low energy temporal difference images data and the respective high energy temporal difference images data acquired during times when the contrast medium was present in the vessel are positive coefficients and the coefficients applied to the low energy and high energy temporal difference images acquired during the pre-contrast period and post-contrast period are negative coefficients such that the sum of all of the coefficients equals zero to effect cancellation of body structure that remains constant in successive images.

6. The method as in claim 1 wherein:

said matched filter coefficients are determined by displaying on a television monitor in sequence the series of low energy temporal difference image data that have been stored and selecting a corresponding zone in successive post-contrast images obtained when said contrast medium was flowing in the vessel which zone is representative of the projected contrast medium intensity in the respective displayed temporal difference images, and also identifying any image in the sequence of displayed post-contrast difference images which exhibits artifacts, such as artifacts due to body motion during an x-ray exposure, of such significance as to justify discarding these images, determining the intensities (h) at said zones in the post-contrast temporal difference images and converting said intensities (h) to matched filter coefficients that are respectively proportional to (h) at successive times (t) at which the temporal images were acquired, storing said coefficients and accessing them in sequence for said multiplication of the low energy temporal images data and said multiplication of the accessed high energy temporal difference images data but setting equal to zero the coefficients for multiplying the low energy temporal difference images that have been identified as containing artifacts and setting to zero the corresponding high energy temporal difference images, and then assigning negative values to some of the coefficients so that all of the coefficients add up to zero.

7. A method of imaging a blood vessel in a body where the period before a bolus of x-ray contrast medium arrives in the vessel is designated the pre-contrast period, the period during which contrast medium is flowing through the vessel is designated the post-contrast period and the period following the latter when the medium has left the vessel is designated the after-post contrast period, and where an x-ray source, when energized, projects a beam through said body to produce x-ray images and including means operative to produce data representative of the images, the method including the following steps:

initiating a sequence of pairs of low and high x-ray energy exposures of the blood vessel which sequence will extend through said pre-contrast period, at least into said post-contrast period and optionally into said after-post-contrast period to produce data representative of the image acquired for each exposure, beginning with the first pair of low and high energy images data, weight these data so that when they are subtracted data representative of soft tissue will cancel out and data representative of bone and contrast medium will remain, then subtract these high and low energy images data in a pair and put the resulting difference image data in storage, and repeat this process of weighting the data for ensuing pairs of high and low energy images, subtracting these data and storing the resulting difference images for the entire exposure sequence so there will be in storage a series of energy difference images, access from storage the series of energy difference image data in succession and multiply these data, respectively, by matched filter coefficients, said matched filter coefficients by which said images data are multiplied being proportional to the projected intensity, (h) of the x-ray contrast medium at times (t) and registered in time with the post-contrast low energy images so that a selected one of the coefficients is applied to the corresponding post-contrast low energy image containing maximum contract medium, and the coefficients applied to the low energy pre-contrast and after-post-contrast images, if any, are selected so that the sum of all of the coefficients equals zero to thereby produce the equivalent of having performed temporal subtraction when the matched filtering step is performed, and when said energy subtracted image data have been multiplied by their respective coefficients, sum the image data resulting from each multiplication to yield data representative of a single hybrid subtracted and matched filtered image that exhibits the contrast medium in the blood vessel.

8. The method as in claim 7 wherein said coefficients are determined by measuring the projected intensity of the contrast medium in a zone in said vessel versus time during the period contrast medium is typically present in the vessel of one or more representative human bodies into which contrast medium has been injected for reaching the vessel corresponding to the vessel of interest in said body being examined, then using coefficients that are proportional to the intensity at any time to multiply the energy difference images data representing images acquired at a corresponding time in said body being examined.

9. The method as in claim 8 wherein the projected intensities (h) in said zone are determined in each of the post-contrast energy difference images, intensity values (h) of zero are assumed for the pre-contrast and any after-post-contrast energy difference images, the average intensity ($\bar{h}$) of the entire set of measured or assumed intensities (h) is determined, and the matched filter coefficient value at a time (t) is set proportional to the difference between the intensity (h) measured or assumed at that time (t) and the average intensity ($\bar{h}$).

10. The method as in claim 7 wherein said coefficients are determined by displaying in sequence the series of energy difference image data that has been stored and selecting a corresponding zone in the successive post-contrast images obtained while said contrast medium was flowing in said vessel which zone is representative of the projected contrast medium intensity in the respective displayed energy difference images, determining the projected intensity (h) in said zone in each of the post-contrast energy difference images and converting the intensities to match filter coefficients that are respectively porportional to (h) at successive times (t) at which the images at the different x-ray energies were acquired, and storing said coefficients and accessing them in sequence for said multiplication of the accessed energy difference images data.

11. The method as in any one of claims 7, 8, 9 or 10 wherein said coefficients applied to the respective energy difference images data acquired during times when the contrast medium was present in the vessel are positive coefficients and the coefficients applied to the energy difference images acquired during the pre-contrast period and post-contrast period are negative coefficients such that the sum of all the coefficients equals zero to effect cancellation of any body structure that remains constant in successive images.

12. The method as in claim 7 wherein:

said matched filter coefficients are determined by displaying on a television monitor in sequence the series of energy difference image data that have been stored and selecting a corresponding zone in successive post-contrast images obtained when said contrast medium was flowing in the vessel which zone is representative of the projected contrast medium intensity in the respective displayed energy difference images, and also identifying any image in the sequence of displayed post-contrast difference images which exhibit artifacts, such as artifacts due to body motion during an x-ray exposure, of such significance as to justify discarding these images, determining the intensities (h) at said zones in the post-contrast energy difference images and converting said intensities (h) to matched filter coefficients that are respectively proportional to (h) at successive times (t) at which the energy difference images were acquired, storing said coefficients and accessing them in sequence for said multiplication of the energy temporal difference images data but setting equal to zero the coefficients for multiplying the energy difference images that have been identified as containing artifacts and setting to zero the corresponding high energy difference images, and then assigning negative values to some of the coefficients so that all of the coefficients add up to zero.

13. A method of imaging a blood vessel in a body where the period before a bolus of x-ray contrast medium arrives in a vessel is designated the pre-contrast period, the period during which contrast medium is flowing through the vessel is designated the post-contrast period and the period following the latter when the medium has left the vessel is designated the after-post-contrast period, and where an x-ray source, when energized, projects a beam through said body to produce x-ray images, and including means operative to produce data representative of the respective images, the method including the following steps:

initiating a sequence of low and high x-ray energy exposures of the blood vessel during the pre-contrast period and continuing the exposures through the post-contrast period and optionally into the after-post-contrast period to thereby provide data representative of the low energy images and high energy images resulting from the exposures with low and high energy x-rays, respectively, integrating the data for a first predetermined number of low energy images in the sequence and storing the result of the integration in a first memory device as the low energy mask image, and also integrating the data for a first same predetermined number of high energy images in the sequence and storing the result of this integration in a second memory device as the high energy mask image, integrating the data for every successive predetermined number of low energy images in the sequence in a third memory device and integrating the data for every successive predetermined number of high energy images in sequence in a fourth memory device, and every time an integration is completed in said third memory device subtract the low energy mask image data in said first memory device from the image data in said third memory device and send the resulting difference image to storage as a low energy temporal difference image, and every time an integration is completed in the fourth memory device subtract the high energy mask image data in said second memory device from the image data in the fourth memory device and send the resulting difference image to storage as a high energy temporal difference image, to thereby have a sequence of alternate low and high energy temporal difference images in storage in which body structures that remain, constant throughout the sequence are cancelled and in which the data representative of the contrast medium and body structures that move during acquiring the sequence of images remains, access from storage the low energy temporal difference images data in succession and the high energy temporal difference images data in succession and multiply the successive low energy temporal difference images data by matched filter coefficients, respectively, and multiply the successive high energy temporal images data by said matched filter coefficients, respectively, said matched filter coefficients by which said images data are multiplied being proportional to the projected intensity, (h) of the x-ray contrast medium at times (t) and registered in time with the post-contrast temporal difference images so that a selected one of the coefficients is applied to the corresponding post-contrast temporal difference image containing maximum contrast medium, and the coefficients applied to the pre-contrast and after-post-contrast temporal difference images, if any, are selected so that the sum of all of the coefficients equals zero.

multiply said low energy temporal difference images data by their respective matched filter coefficients and sum the results and multiply said high energy temporal difference images data by said coefficients and sum the results, to thereby produce one set of data representative of a matched filtered low energy temporal difference image and another set of data representative of a matched filtered high energy temporal difference image, multiply said one low energy temporal difference image data set by a constant ($k_L$) and said other high energy temporal image data set by a constant ($k_H$), said constants being so chosen that when said sets of multiplied image data are subtracted data representative of motion of a specific material in the body is cancelled, and after the preceding multiplications, subtracting the resulting sets of data to yield a set of data representative of the image of the contrast medium in said blood vessel.

14. The method as in claim 13 wherein said coefficients are determined by measuring the projected intensity of the contrast medium at a zone in said vessel versus time over the period during which contrast medium is typically present in the vessel of one or more representative human bodies into which contrast medium has been injected for reaching the vessel corresponding to the vessel of interest in said body being examined, then using coefficients that are proportional to the intensity at any time to multiply the low energy temporal images data and the high energy temporal difference images data representing images acquired at a corresponding time.

15. The method as in claim 13 wherein said coefficients are determined by displaying in sequence the series of temporal difference images data that has been stored and selecting a corresponding zone in the successive post-contrast images obtained while said contrast medium was flowing in said vessel which zone is representative of the projected contrast medium intensity in the respective displayed temporal difference images, determining the intensities (h) at said zones in each of the post-contrast temporal difference images and converting said intensities (h) to match filter coefficients that are respectively proportional to (h) at successive times (t) at which the temporal images were acquired, and storing said coefficients and accessing them in sequence for said multiplication of the accessed low energy temporal difference image data and said multiplication of the accessed high energy temporal difference image data.

16. The method as in claim 13 wherein the intensities (h) at said zones are determined in each of the post-contrast temporal difference images, intensity values (h) of zero are assumed for the pre-contrast and after-post-contrast temporal difference images, if any, the average intensity ($\bar{h}$) of the entire set of measured or assumed intensities is determined, and the matched filter coefficient at a time (t) is set proportional to the difference between the intensity (h) measured or assumed at that time (t) and the average intensity ($\bar{h}$).

17. The method as in any one of claims 13, 14, 15 or 16 wherein said coefficients applied to the respective low energy temporal difference images data and the respective high energy temporal difference images data acquired during times when the contrast medium was present in the vessel are positive coefficients and the coefficients applied to the low energy and high energy temporal difference images acquired during the pre-contrast period and post-contrast period are negative coefficients such that the sum of all of the coefficients equals zero to effect cancellation of any body structure that remains constant in successive images.

18. The method as in claim 13 wherein:

said matched filter coefficients are determined by displaying on a television monitor in sequence the series of low energy temporal difference image data that have been stored and selecting a corresponding zone in successive post-contrast images obtained when said contrast medium was flowing in the vessel which zone is representative of the projected contrast medium intensity in the respective displayed temporal difference images, and also identifying any images in the sequence of displayed post-contrast difference images which exhibit artifacts, such as artifacts due to body motion during an x-ray exposure, of such significance as to justify discarding these images, determining the intensities (h) at said zones in the post-contrast temporal difference images and converting said intensities (h) to matched filter coefficients that are respectively proportional to (h) at successive times (t) at which the temporal images were acquired, storing said coefficients and accessing them in sequence for said multiplication of the low energy temporal images data and said multiplication of the accessed high energy temporal difference images data but setting equal to zero the coefficients for multiplying the low energy temporal difference images that have been identified as containing artifacts and setting to zero the corresponding high energy temporal difference images, and then assigning negative values to some of the coefficients so that all of the coefficients add up to zero.

19. A method of imaging a blood vessel in a body where the period before a bolus of x-ray contrast medium arrives in the vessel is designated the pre-contrast period, the period during which contrast medium is flowing through the vessel is designated the post-contrast period and the period following the latter when the medium has left the vessel is designated the after-post-contrast period, and where an x-ray source, when energized, projects a beam through said body to product x-ray images and means operative to produce data representative of the images, the method including the following steps:

initiating a sequence of pairs of low and high x-ray energy exposures of the blood vessel which sequence will extend through a pre-contrast period, at least into the post-contrast period and optionally into said after-post-contrast period to produce data representative of the image acquired for each exposure, alternately integrate the data for a predetermined number of the successive low energy images and integrate the date for the same number of successive alternate high energy images and each time a pair of low and high energy integrated image data are completed weight the integrated low and high energy image data and then subtract the integrated low and high energy data to yield the data representing an energy difference image and send the difference image to storage and repeat the process of integrating successive series of low and high energy images and of weighting, of subtracting and of storing for the entire exposure sequence so as to have in storage a series of energy subtracted image data in which data representative of soft tissue is substantially cancelled out and data representative of bone and x-ray contrast medium remain, access from storage the series of energy difference image data in succession and multiply these data, respectively, by matched filter coefficients, said matched filter coefficients by which said images data are multiplied being proportional to the projected intensity, (h), of the x-ray contrast medium at times (t) and registered in time with the post-contrast temporal difference images so that a selected one of the coefficients is applied to the corresponding post-contrast temporal difference image containing maximum contrast medium, and the coefficients applied to the pre-contrast and after post-contrast temporal difference images, if any, are selected so that the sum of all of the coefficients equals zero to thereby produce the equivalent of having performed temporal subtraction when the matched filtering step is performed, and multiply said energy difference image data by their respective coefficients and sum the image data resulting from each multiplication to yield the data representative of a single hybrid subtracted and matched filtered image that exhibits substantially only the contrast medium in the blood vessel.

20. The method as in claim 19 wherein said coefficients are determined by measuring the projected intensity of the contrast medium at a zone in said vessel versus time over the period during which contrast medium is typically present in the vessel of one or more representative human bodies into which contrast medium has been injected for reaching the vessel corresponding to the vessel of interest in said body being examined, then using coefficients that are proportional to the intensity at any time to multiply the energy difference images data representing images acquired at a corresponding time in said body being examined.

21. The method as in claim 19 wherein said coefficients are determined by displaying in sequence the series of energy difference image data that has been stored and selecting a corresponding zone in the successive post-contrast images obtained while said contrast medium was flowing in said vessel which zone is representative of the projected contrast medium intensity in the respective displayed energy difference images, determining the intensities (h) at said zones in each of the post-contrast energy difference images and converting said intensities (h) to match filter coefficients that are proportional to (h) at successive times (t) at which the energy difference images were acquired, and storing said coefficients and accessing them in sequence for said multiplication of the accessed energy difference image data.

22. The method as in claim 21 wherein the intensities (h) at said zones are determined in each of the post-contrast energy difference images, intensities (h) of zero are assumed for the pre-contrast and after-post-contrast energy difference images, the average intensity $(\bar{h})$ of the entire set of measured or assumed intensities (h) is determined, and the matched filter coefficient at a time (t) is set proportional to the difference between the intensity (h) measured or assumed at that time (t) and the average intensity $(\bar{h})$.

23. The method as in any of claims 19, 20, 21 or 22 wherein said coefficients applied to the respective energy difference images data acquired during times when the contrast medium was present in the vessel are positive coefficients and the coefficients applied to the energy difference images acquired during the pre-contrast period and post-contrast period, if any, are negative coefficients such that the sum of all the coefficients equals zero to effect cancellation of any body structure that remains constant in successive images.

24. The method as in claim 19 wherein:
said matched filter coefficients are determined by displaying on a television monitor in sequence the series of energy difference image data that have been stored and selecting a corresponding zone in successive post-contrast images obtained when said contrast medium was flowing in the vessel which zone is representative of the projected contrast medium intensity in the respective displayed energy difference images, and also identifying any image in the sequence of displayed post-contrast difference images which exhibit artifacts, such as artifacts due to body motion during an x-ray exposure, of such significance as to justify discarding these images, determining the intensities (h) at said zones in the post-contrast energy difference images and converting said intensities (h) to matched filter coefficients that are respectively proportional to (h) at successive times (t) at which the energy difference images were acquired, storing said coefficients and accessing them in sequence for said multiplication of the accessed energy difference images data but setting equal to zero the coefficients for multiplying the energy difference images that have been identified as containing artifacts and setting to zero the corresponding energy difference images, and then assigning negative values to some of the coefficients so that all of the coefficients add up to zero.

25. A method of imaging a blood vessel in a body where the period before a bolus of x-ray contrast medium arrives in the vessel is designated the pre-contrast period, the period during which contrast medium is flowing through the vessel is designated the post-contrast period and the period following the latter when the medium has left the vessel is designated the after-post-contrast period, and where an x-ray source, when energized, projects a beam through said body to produce x-ray images, and including means operative to produce data representative of the respective images, the method including the following steps:

- initiating a sequence of pairs of low and high x-ray energy exposures of said blood vessel during the pre-contrast period and continuing the exposures into the post-contrast and optionally into the after-post-contrast periods, as each low and high energy image is acquired store the data sets representative of the images for subsequent sequential access from storage, use one or an integration of a predetermined number of data sets representative of pre-contrast low energy images as a low energy mask image, and use one or an integration of the same predetermined number of pre-contrast high energy images, respectively, as a high energy mask image, subtract the low energy mask image data set from each subsequent one or integration of low energy images data sets, respectively, and alternately subtract the high energy mask image data set from each subsequent one or integration of high energy data sets, respectively, for the entire exposure sequence to thereby yield an alternating series of low and high temporal difference images in which data representing structures that remain constant through the sequence of images are cancelled and letting data representative of said contrast medium and representative of structures that change during acquisition of the series of images remain, multiply the successive low energy temporal difference images data by matched filter coefficients, respectively, and multiply the successive high energy temporal images data by matched filter coefficients, respectively, said matched filter coefficients by which said images are multiplied being proportional to the projected intensity, (h) of the x-ray contrast medium at times (t) and substantially registered in time with the post-contrast temporal difference images so that a selected one of the coefficients is applied to the corresponding post-contrast temporal difference image containing maximum contrast medium, and the coefficients applied to the pre-contrast and after-post-contrast temporal difference images, if any, are selected so that the sum of all of the coefficients equals zero, multiply said low energy temporal difference images data by the respective matched filter coefficients and sum the results and multiply said high energy temporal difference images data by said coefficients and sum the results, to thereby produce one set of data representative of a matched filtered low energy temporal difference image and another set of data representative of a matched filtered high energy temporal difference image, multiply said one low energy temporal difference image data set by a constant ($k_L$) and said other high energy temporal image data set by a constant ($k_H$), said constants being so chosen that when said sets of multiplied image data are subtracted data representative of motion of a specific material in the body are cancelled, and after the preceding multiplications, subtracting the resulting sets of data to yield a set of data representative of the image of the contrast medium in said blood vessel.

26. The method as in claim 25 wherein said coefficients are determined by measuring the projected intensity of the contrast medium at a zone in said vessel versus time over the interval during which contrast medium is typically present in the vessel of one or more representative human bodies into which contrast medium has been injected for reaching the vessel corresponding to the vessel of interest in said body being examined, then using coefficients that are proportional to the intensity at any time to multiply the low energy temporal difference images data and the high energy temporal difference images data representing images acquired at a corresponding time.

27. The method as in claim 25 wherein said coefficients are determined by displaying in sequence the series of temporal difference images data that has been stored and selecting a corresponding zone in the successive post-contrast images obtained while said contrast medium was flowing in said vessel which zone is representative of the projected contrast medium intensity in the respective displayed temporal difference images, determining the intensities (h) at said zones in each of the post-contrast temporal difference images and converting said intensities (h) to match filter coefficients that are respectively proportional to (h) at successive times (t) at which the temporal images were acquired, and storing said coefficients and accessing them in sequence for said multiplication of the accessed low energy temporal difference image data and said multiplication of the accessed high energy temporal difference image data.

28. The method as in claim 27 wherein the intensities (h) at said zones are determined in each of the post-contrast temporal difference images, intensity values (h) of zero are assumed for the pre-contrast and after-postcontrast temporal difference images, if any, the average intensity ($\bar{h}$) of the entire set of measured or assumed intensities (h) is determined, and the matched filter coefficient value at a time (t) is set proportional to the difference between the intensity (h) measured or assumed at that time (t) and the average intensity ($\bar{h}$).

29. The method as in any one of claims 25, 26, 27 or 28 wherein said coefficients applied to the respective low energy temporal difference images data and the respective high energy temporal difference images data acquired during times when the contrast medium was present in the vessel are positive coefficients and the coefficients applied to the low energy and high energy temporal difference images acquired during the pre-contrast period and post-contrast period are negative coefficients such that the sum of all of the coefficients equals zero to effect cancellation of any body structure that remains constant in successive images.

30. The method as in claim 25 wherein:
said matched filter coefficients are determined by displaying on a television monitor in sequence the series of low energy temporal difference image data that have been stored and selecting a corresponding zone in successive post-contrast images obtained when said contrast medium was flowing in the vessel which zone is representative of the projected contrast medium intensity in the respective displayed temporal difference images, and also identifying any in the sequence of displayed post-contrast difference images which exhibit artifacts, such as artifacts due to body motion during an x-ray exposure, of such significance as to justify discarding these images, determining the intensities (h) at said zones in the post-contrast temporal difference images and converting said intensities (h) to matched filter coefficients that are respectively proportional to (h) at successive times (t) at which the temporal images were acquired, storing said coefficients and accessing them in sequence for said multiplication of the low energy temporal images data and said multiplication of the accessed high energy temporal difference images data but setting equal to zero the coefficients for multiplying the low energy temporal difference images that have been identified as containing artifacts and setting to zero the corresponding high energy temporal difference images, and then assigning negative values to some of the coefficients so that all of the coefficients add up to zero.

31. A method of imaging a blood vessel in a body where the period before a bolus of x-ray contrast medium arrives in the vessel is designated the pre-contrast period, the period during which contrast medium is flowing through the vessel is designated the post-contrast period and the period following the latter when the medium has left the vessel is designated the after-post-contrast period, and where an x-ray source, when energized, projects a beam through said body to produce x-ray images and including means operative to produce data representative of the images, the method including the following steps:

initiating a sequence of low an high x-ray energy exposures of the blood vessel which sequence will extend through a pre-contrast period, into the post-contrast period and optionally into an after-post-contrast period to produce data sets representative of the images acquired for each exposure, and put the sequence of low and high energy image data sets in storage as they are acquired, access from storage and take pairs of low and high energy image data where each pair includes one of a low energy image data set or an integration of a predetermined number of successive low energy image data sets and each pair also includes one of a corresponding high energy image data set or a corresponding integration of the same predetermined number of successive high energy image data sets, respectively, and weight these data in each pair so that when the low energy data and high energy data in a pair are subtracted, energy subtracted image data will result in which data representative of soft tissue will substantially cancel out and data representative of bone and contrast medium will remain, repeat the steps of taking pairs of low and high energy image data, of weighting the data and of subtracting the pairs of data for the entire exposure sequence to produce a sequence of energy subtracted images, multiply these data by respective matched filter coefficients, said matched filter coefficients by which said images data are multiplied being proportional to the projected intensity, (h) of the x-ray contrast medium at times (t) and registered in time with the post-contrast temporal difference images so that a selected one of the coefficients is applied to the corresponding post-contrast temporal difference image containing maximum contrast medium, and the coefficients applied to the pre-contrast temporal difference images and after-post-contrast temporal difference images are selected so that the sum of all of the coefficients equals zero to thereby produce the equivalent of having performed temporal subtraction when the matched filtering step is performed, and multiply said energy difference images data by their respective coefficients and sum the image data resulting from each multiplication to yield the data representative of a single hybrid subtracted and matched filtered image that exhibits substantially only the contrast medium in the blood vessel.

32. The method as in claim 31 wherein said coefficients are determined by measuring the projected intensity of the contrast medium at a zone in said vessel versus time over the period during which contrast medium is typically present in the vessel of one or more representative human bodies into which contrast medium has been injected, for reaching a vessel corresponding to the vessel of interest in said body being examined, then using coefficients that are proportional to the intensity at any time to multiply the energy difference images data representing images acquired at a corresponding time.

33. The method as in claim 31 wherein said coefficients are determined by displaying in sequence the series of energy difference image data that has been stored and selecting a corresponding zone in the successive post-contrast images obtained while said contrast medium was flowing in said vessel which zone is representative of the projected contrast medium intensity in the respective displayed energy difference images, determining the intensities (h) at said zones in each of the post-contrast energy difference images and converting said intensities (h) to match filter coefficients that are respectively proportional to (h) at successive times (t) at which the energy images were acquired, and storing said coefficients and accessing them in sequence for said multiplication of the accessed energy difference images data.

34. The method as in claim 33 wherein the intensities (h) at said zones are determined in each of the post-contrast energy difference images, intensities (h) of zero are assumed for the pre-contrast and after-post-contrast energy difference images, the average intensity ($\bar{h}$) of the entire set of measured or assumed intensities (h) is determined, and the matched filter coefficient value at a time (t) is set proportional to the difference between the intensity (h) measured or assumed at that time (t) and the average intensity ($\bar{h}$).

35. The method as in any one of claims 32, 33 or 34 wherein said coefficients applied to the respective energy difference images data acquired during times when the contrast medium was present in the vessel are positive coefficients and the coefficients applied to the energy difference images acquired during the pre-contrast period and post-contrast period are negative coefficients such that the sum of all the coefficients equals zero to effect cancellation of any body structure that remains constant in successive images.

36. The method as in claim 31 wherein:
said matched filter coefficients are determined by displaying on a television monitor in sequence the series of energy difference image data that have been stored and selecting a corresponding zone in successive post-contrast images obtained when said contrast medium was flowing in the vessel which zone is representative of the projected contrast medium intensity in the respective displayed energy difference images, and also identifying any image in the sequence of displayed post-contrast difference images which exhibit artifacts, such as artifacts due to body motion during an x-ray exposure, of such significance as to justify discarding these images, determining the intensities (h) at said zones in the post-contrast energy difference images and converting said intensities (h) to matched filter coefficients that are respectively proportional to (h) at successive times (t) at which the energy difference images were acquired, storing said coefficients and accessing them in sequence for said multiplication of the energy difference images data but setting equal to zero the coefficients for multiplying the energy difference images that have been identified as containing artifacts and then assigning negative values to some of the coefficients so that all of the coefficients add up to zero.

37. A method of imaging a blood vessel in a body where the period before a bolus of x-ray contrast medium arives in the vessel is designated the pre-contrast period, the period during which contrast medium is flowing through the vessel is designated the post-contrast period and the period following the latter when the medium has left the vessel is designated the after-post-contrast period, and where an x-ray source, when energized, projects a beam through said body to produce x-ray images, the method including the following steps:

initiating a sequence of low and high x-ray energy exposures of the blood vessel during the pre-contrast period and continuing the exposures through the post-contrast and optionally into the after-post-contrast periods to thereby provide data representative of the images resulting from the exposures, the data representative of an image resulting from one pre-contrast exposure at said low x-ray energy being designated the low energy mask image data and the data resulting from a pre-contrast exposure at said high x-ray energy being designated the high energy mask image data, after the low and high energy mask image data are acquired subtract the low energy mask image data from the data for each of the ensuing low energy images and send the resulting series of low energy temporal difference image data to storage as they are produced and alternately subtract the high energy mask image data from the data for each of the ensuing high energy images and send the resulting series of high energy temporal difference image data to storage as they are produced, said subtraction causing body structure that remain constant throughout the sequence of images to be cancelled and letting data representative of said contrast medium and body structure that changes remain, access from storage successive pairs of low energy and high energy image data and weight the data comprising each pair and then subtract the data for one image in the pair from the other to yield a series of energy subtracted image data sets wherein substantially only data representative of motion of a specific structure in the body are cancelled, multiply the energy subtracted images data by matched filter coefficients, said matched filter coefficients by which said images data are multiplied being proportional to the projected intensity, (h) of the x-ray contrast medium at times (t) and registered in time with the post-contrast temporal difference images so that a selected one of the coefficients is applied to the corresponding post-contrast temporal difference image containing maximum contrast medium, and the coefficients applied to the pre-contrast temporal difference images and after-post-contrast temporal difference images are selected so that the sum of all of the coefficients equals zero to thereby produce the equivalent of having performed temporal subtraction when the matched filtering step is performed, and multiply said energy difference image data by their respective coefficients and sum the image data resulting from each multiplication to yield the data representative of a single hybrid subtracted and matched filtered image that exhibits only the contrast medium in the blood vessel.

38. The method as in claim 37 wherein said coefficients are determined by measuring the projected intensity of the contrast medium at a zone in said vessel versus time during the time in which contrast medium is typically present in the vessel of one or more representative human bodies into which contrast medium has been injected for reaching a vessel corresponding to the vessel of interest in said body being examined, then using coefficients that are proportional to the intensity at any time to multiply the low energy temporal images data and the high energy temporal difference images data representing images acquired at a corresponding time in said body being examined.

39. The method as in claim 37 wherein said coefficients are determined by displaying in sequence the series of temporal difference image data that has been stored and selecting a corresponding zone in the successive post-contrast images obtained while said contrast medium was flowing in said vessel which zone is representative of the projected contrast medium intensity in the respective displayed temporal difference images, determining the intensities (h) at said zones in each of the post-contrast temporal difference images and converting said intensities (h) to match filter coefficients that are respectively proportional to (h) at successive times (t) at which the temporal images were acquired, and storing said coefficients and accessing them in sequence for said multiplication of the accessed low energy temporal difference image data and said multiplication of the accessed high energy temporal difference image data.

40. The method as in claim 39 wherein the intensities (h) at said zones are determined in each of the post-contrast temporal difference images, intensities (h) of zero are assumed for the pre-contrast and after-post-contrast temporal difference images, the average intensity ($\bar{h}$) of the entire set of measured or assumed intensities (h) is determined, and the matched filter coefficient value at a time (t) is set proportional to the difference between the intensity (h) measured or assumed at that time (t) and the average intensity ($\bar{h}$).

41. The method as in any one of claims 37, 38, 39 or 40 wherein said coefficients applied to the respective low energy temporal difference images data and the respective high energy temporal difference images data acquired during times when the contrast medium was present in the vessel are positive coefficients and the coefficients applied to the low energy and high energy temporal difference images acquired during the pre-contrast period and post-contrast period are negative coefficients such that the sum of all the coefficients equals zero to effect cancellation of any body structure that remains constant in successive images.

42. The method as in claim 37 wherein:

said matched filter coefficients are determined by displaying on a television monitor in sequence the series of low energy temporal difference image data that have been stored and selecting a corresponding zone in successive post-contrast images obtained when said contrast medium was flowing in the vessel which zone is representative of the projected contrast medium intensity in the respective displayed temporal difference images, and also identifying any image in the sequence of displayed post-contrast difference images which exhibit artifacts, such as artifacts due to body motion during an x-ray exposure, of such significance as to justify discarding these images, determining the intensities (h) at said zones in the post-contrast temporal difference images and converting said intensities (h) to matched filter coefficients that are respectively proportional to (h) at successive times (t) at which the temporal images were acquired, storing said coefficients and accessing them in sequence for said multiplication of the low energy temporal images data and said multiplication of the accessed high energy temporal difference images data but setting equal to zero the coefficients for multiplying the low energy temporal difference images that have been identified as containing artifacts and setting to zero the corresponding high energy temporal difference images, and then assigning negative values to some of the coefficients so that all of the coefficients add up to zero.

43. A method of imaging a blood vessel in a body where the period before a bolus of x-ray contrast medium arrives in the vessel is designated the pre-contrast period, the period during which contrast medium is flowing through the vessel is designated the post-contrast period and the period following the latter when the medium has left the vessel is designated the after-post-contrast period, and where an x-ray source, when energized, projects a beam through said body to produce x-ray images, and including means operative to produce data representative of the respective images, the method including the following steps:

initiating a sequence of closely successive pairs of low and high x-ray energy exposures of the blood vessel during the pre-contrast period and continuing the exposures through the post-contrast and after-post-contrast periods to thereby provide data representative of the images resulting from the exposures, multiply the data representative of each low energy image in a pair by a weighting factor ($k_1$) and multiply the data representative of each high energy image in the same pair by a weighting factor ($k_2$), and perform the multiplications in the order in which the images are acquired, said weighting factors being chosen so that when the weighted data for the images in each pair are subtracted the data representative of soft tissue will be cancelled and the data representative of bone and the x-ray contrast medium will remain, subtract the weighted data for one of the images in each pair from the weighted data for the other to thereby yield a series of energy subtracted images data, input the series of energy subtracted images data simultaneously to first and second recursive filter circuits which each have different time constants (K and K') and each of which has a dc response equal to 1 so that when the results of recursive filtering in the one circuit are subtracted from the results in the other the dc components of the image data will cancel to thereby achieve the equivalent of temporal image subtraction which is characterized by canceling data that is representative of body structure that is constant in the sequence of images and letting the data representative of the contrast medium remain, finally subtract the results of recursive filtering in one circuit from the results in the other to yield a single difference image data set for an image that can be displayed.

* * * * *

UNITED STATES PATENT AND TRADEMARK OFFICE
CERTIFICATE OF CORRECTION

PATENT NO. : 4,542,459
DATED : September 17, 1985
INVENTOR(S) : Stephen J. Riederer It is certified that error appears in the above-identified patent and that said Letters Patent are hereby corrected as shown below:

Claim 1, column 26, line 29 change "initializing" to ---initiating---.

Claim 3, column 27 line 47 change spelling of "sucessive" to ---successive---.

Claim 7, column 28, line 57 "after-post contrast" should read ---after-post-contrast---.

Claim 10, column 30, line 1 after "intensities" insert ---(h)---.

Claim 37, column 39, line 58 change "arives" to ---arrives---.

Signed and Sealed this

Second Day of September 1986

[SEAL]

Attest:

DONALD J. QUIGG

*Attesting Officer*　　*Commissioner of Patents and Trademarks*